(12) United States Patent
Lepek et al.

(10) Patent No.: US 11,785,926 B2
(45) Date of Patent: Oct. 17, 2023

(54) METHOD FOR SEX SORTING OF MOSQUITOES AND APPARATUS THEREFOR

(71) Applicant: Senecio Ltd., Kfar-Saba (IL)

(72) Inventors: Hanan Lepek, Kfar-Saba (IL); Tamir Nave, Kiryat-Ono (IL); Yoram Fleischmann, Kibbutz Lehavot Haviva (IL); Rom Eisenberg, Kfar-Saba (IL); Baruch E. Karlin, Haifa (IL); Itamar Tirosh, RaAnana (IL)

(73) Assignee: Senecio Ltd., Kfar-Saba (IL)

( * ) Notice: Subject to any disclaimer, the term of this patent is extended or adjusted under 35 U.S.C. 154(b) by 0 days.

(21) Appl. No.: 17/067,694

(22) Filed: Oct. 11, 2020

(65) Prior Publication Data
US 2021/0022326 A1 Jan. 28, 2021

Related U.S. Application Data

(62) Division of application No. 16/479,648, filed as application No. PCT/IL2018/050081 on Jan. 22, 2018.

(Continued)

(51) Int. Cl.
*A01K 67/033* (2006.01)
*A01K 1/03* (2006.01)
(Continued)

(52) U.S. Cl.
CPC .............. *A01K 67/033* (2013.01); *A01K 1/03* (2013.01); *A01M 1/026* (2013.01); *A01M 1/223* (2013.01);
(Continued)

(58) Field of Classification Search
CPC ...... A01K 67/033; A01K 1/03; A01K 29/005; G05B 17/00; G06T 1/20; A01M 1/026;
(Continued)

(56) References Cited

U.S. PATENT DOCUMENTS 10,278,368 B1 * 5/2019 Peeters ................ A01K 29/005
11,395,474 B2 7/2022 Hall et al.
(Continued)

FOREIGN PATENT DOCUMENTS

WO WO 2009/067089 5/2009

OTHER PUBLICATIONS

International Preliminary Report on Patentability dated Jan. 31, 2020 From the International Preliminary Examining Authority Re. Application No. PCT/IL2018/050738. (27 Pages).
(Continued)

*Primary Examiner* — John W Lee

(57) ABSTRACT

Method and apparatus for mechanical sex-sorting of mosquitoes by extracting a class of mosquitoes from unsorted mosquitoes comprises obtaining unsorted mosquitoes, obtaining images of individual mosquitoes in a stationary phase, electronically classifying the individuals from the images into male mosquitoes and/or female mosquitoes, and possibly also unclassified objects; obtaining co-ordinates of individuals of at least one of the male mosquito and female mosquito classifications, and using a robot arm to reach an (Continued)

individual identified by the obtained coordinates to store or remove the individuals, thereby to provide sex-sorted mosquitoes.

40 Claims, 18 Drawing Sheets

Related U.S. Application Data

(60) Provisional application No. 62/533,242, filed on Jul. 17, 2017, provisional application No. 62/529,057, filed on Jul. 6, 2017, provisional application No. 62/458,065, filed on Feb. 13, 2017, provisional application No. 62/449,050, filed on Jan. 22, 2017.

(51) Int. Cl.
| | |
|---|---|
| *A01M 1/02* | (2006.01) |
| *A01M 1/22* | (2006.01) |
| *G01N 35/00* | (2006.01) |
| *G05B 17/00* | (2006.01) |
| *G06N 3/08* | (2023.01) |
| *G06T 1/20* | (2006.01) |
| *G06V 10/764* | (2022.01) |
| *G06V 10/82* | (2022.01) |
| *G06V 20/69* | (2022.01) |
| *G06V 40/10* | (2022.01) |
| *A01K 29/00* | (2006.01) |
| *G06N 3/045* | (2023.01) |

(52) U.S. Cl.
CPC ......... *G01N 35/0099* (2013.01); *G05B 17/00* (2013.01); *G06N 3/045* (2023.01); *G06N 3/08* (2013.01); *G06T 1/20* (2013.01); *G06V 10/764* (2022.01); *G06V 10/82* (2022.01); *G06V 20/698* (2022.01); *G06V 40/10* (2022.01)

(58) Field of Classification Search
CPC .............. A01M 1/223; G01N 35/0099; G06K 9/00362; G06K 9/00147; G06K 9/6273; G06N 3/0454; G06N 3/08
See application file for complete search history.

(56) References Cited

U.S. PATENT DOCUMENTS

| | | | | |
|---|---|---|---|---|
| 2005/0025357 | A1* | 2/2005 | Landwehr | A01M 3/005 382/224 |
| 2013/0222410 | A1* | 8/2013 | Kameyama | H04N 13/344 345/589 |
| 2015/0023566 | A1* | 1/2015 | Fryshman | A01M 3/00 382/110 |
| 2018/0092339 | A1* | 4/2018 | Massaro | G06Q 50/02 |
| 2018/0121764 | A1* | 5/2018 | Zha | G06F 18/2413 |
| 2020/0154685 | A1 | 5/2020 | Lepek et al. | |
| 2020/0154686 | A1 | 5/2020 | Lepek et al. | |
| 2020/0281164 | A1 | 9/2020 | Lepek et al. | |

OTHER PUBLICATIONS

Search Report and Written Opinion dated Nov. 2, 2020 From the Intellectual Property Office of Singapore, IPOS Re. Application No. 11201906740Y. (11 Pages).

Notification of Office Action and Search Report dated Nov. 10, 2021 From the State Intellectual Property Office of the People's Republic of China Re. Application No. 2018800075.86.0 and Its Translation of Office Action Into English. (9 Pages).

Official Action dated Dec. 24, 2021 from US Patent and Trademark Office Re. U.S. Appl. No. 16/479,648. (30 pages).

Restriction Official Action dated Aug. 27, 2021 from the US Patent and Trademark Office Re. U.S. Appl. No. 16/479,649. (7 pages).

Examination Report Under Sections 12 & 13 of the Patents Act, 1970 and the Patents Rules, 2003 dated Jan. 3, 2022 From the Government of India, Intellectual Property India, Patents. Designs, Trade Marks, Geographical Indications, The Patent Office Re. Application No. 201947029980. (5 Pages).

Final Official Action dated Jul. 12, 2022 from US Patent and Trademark Office Re.U.S. Appl. No. 16/479,648. (16 pages).

Interview Summary dated Jan. 10, 2023 from the US Patent and Trademark Office Re. U.S. Appl. No. 16/479,648. (2 pages).

Official Action dated Feb. 15, 2023 from US Patent and Trademark Office Re. U.S. Appl. No. 16/479,648. (13 pages).

Examination Report dated Mar. 16, 2023 From the Australian Government, IP Australia Re. Application No. 2018209481. (5 Pages).

* cited by examiner

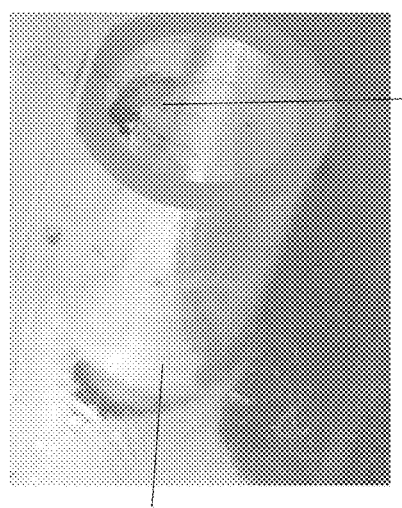
Fig. 5
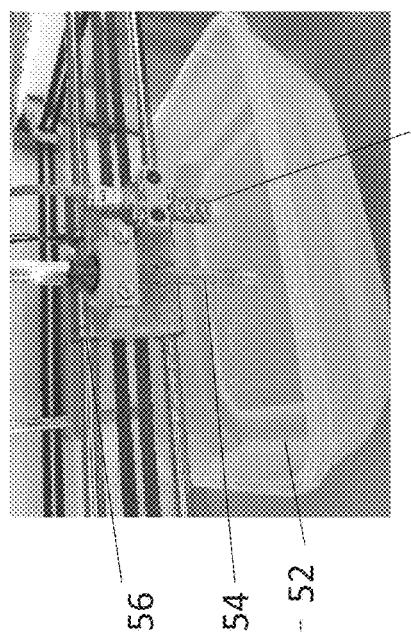
Fig. 4
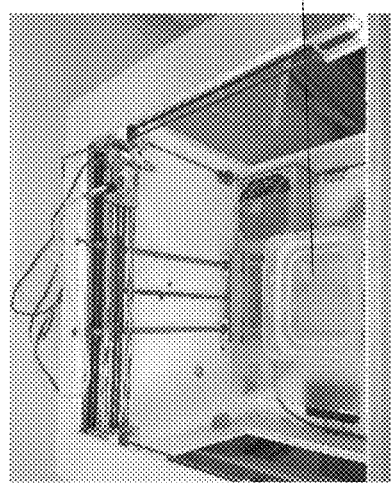
Fig. 3
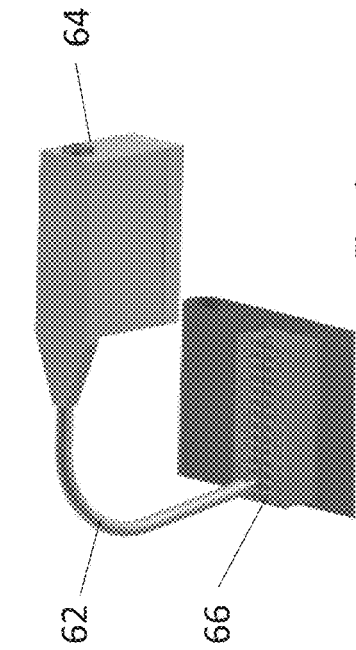
Fig. 7
Fig. 6

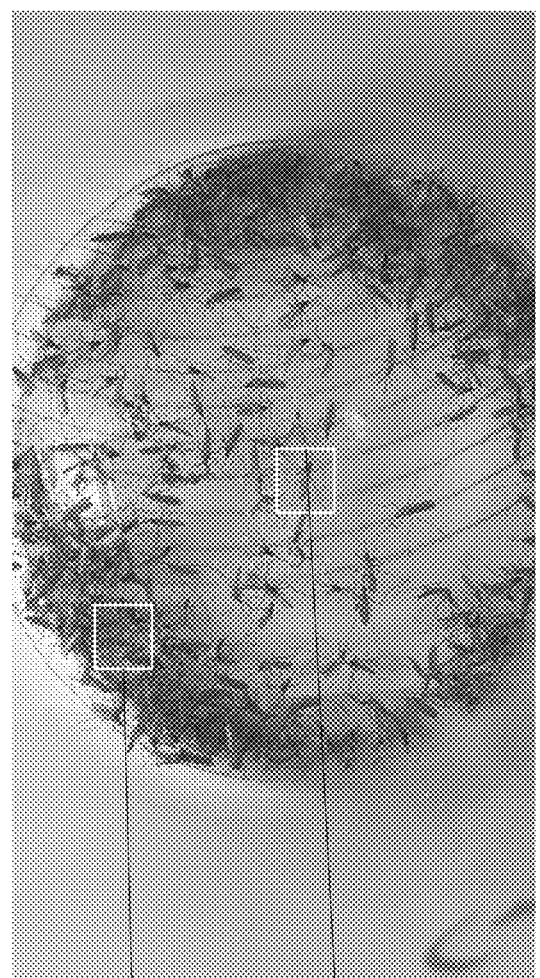
Fig. 20
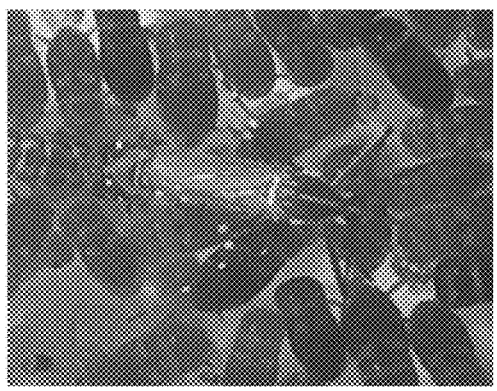
Fig. 18
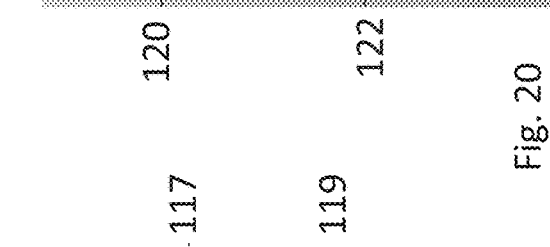
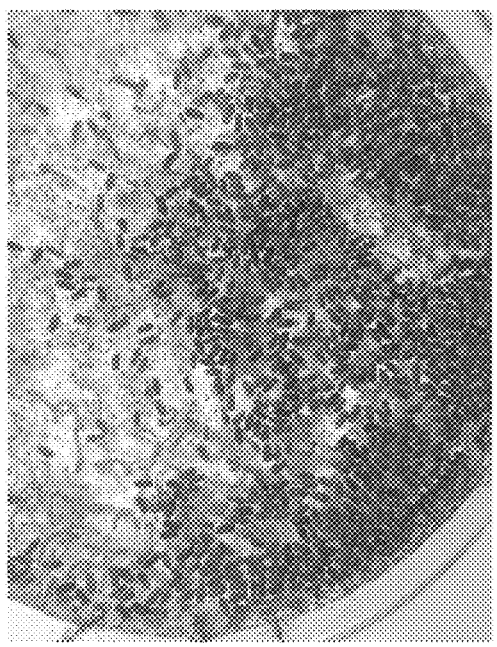
Fig. 17
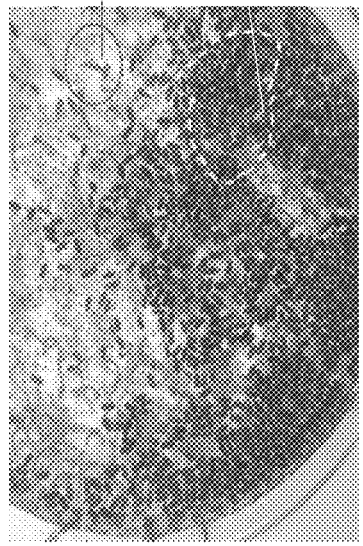
Fig. 19

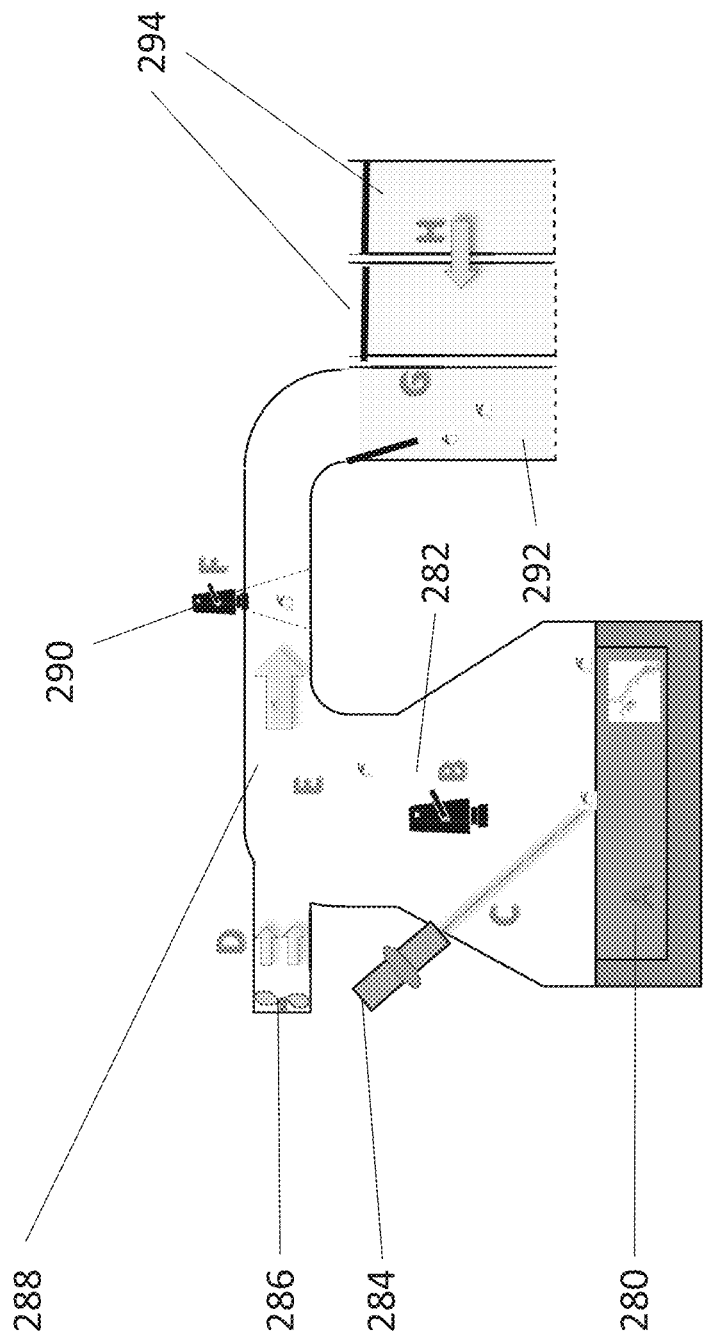

METHOD FOR SEX SORTING OF MOSQUITOES AND APPARATUS THEREFOR

RELATED APPLICATIONS

This application is a division of U.S. patent application Ser. No. 16/479,648 filed on Jul. 22, 2019, which is a National Phase of PCT Patent Application No. PCT/IL2018/050081 having International Filing Date of Jan. 22, 2018, which claims the benefit of priority under 35 USC § 119(e) of U.S. Provisional Patent Application Nos. 62/533,242 filed on Jul. 17, 2017, 62/529,057 filed on Jul. 6, 2017, 62/458,065 filed on Feb. 13, 2017 and 62/449,050 filed on Jan. 22, 2017.

The contents of the above applications are all incorporated by reference as if fully set forth herein in their entirety.

FIELD AND BACKGROUND OF THE INVENTION

The present invention, in some embodiments thereof, relates to sex sorting of mosquitoes and, more particularly, but not exclusively, to a method and apparatus for providing sorted male mosquitoes.

To date, mosquito SIT (Sterile Insect Technique) has proved itself in small scale projects around the globe, as a promising and effective tool for fighting mosquito-borne diseases. The idea is to release male mosquitoes with unique characteristics such that their offspring do not evolve, or the distributed males are sterile such that there will not be any offspring.

Small scale pilots, in which a few million male mosquitoes were released on small area, were performed by different research institutions and companies, all demonstrated reduction in mosquito population in that area weeks after deploying the engineered male mosquitoes on a weekly basis.

In order to treat large areas, millions of mosquitoes are needed to be produced on a daily basis.

However, the operational costs associated with the labor intensive involved in the rearing and handling process today prevent the mosquito SIT from scaling up. The specific steps in the rearing process we are referring to are:

1. The sex sorting procedure. It is required to release males only, as opposed to releasing females when the target goal is to replace the local population and create a new type of mosquito population. The mosquitoes need to be sorted between females and males, and only males should be in the release boxes sent to the field for release.
2. The loading of the mosquitoes into the release boxes. Today, the common procedure is to place pupa (together with water) inside the release boxes. As each release box may contain in the order of 700-1500 mosquitoes, the workers need to transfer the pupa from other larger containers, and measure the quantity transferred, although resolution to a single mosquito is not required. Transferring 1,000 pupa into a release box at a time when millions of pupa per day are needed is highly intensive work requiring time and people. The costs are too high for large scale operations.

There is on-going research to optimize the sorting process. However, most systems to date, have tried to sort while in the pupa stage (based on weight, size, color). Other attempts have involved zapping the female mosquitoes while they are adults.

A problem is that the adult mosquito can be very active, and thus from the moment you classified its sex until you manage to do something it may have moved or flown away. Also having other mosquitoes in the field of view may obscure the vision sensor. Sorting at the pupa, may lead to large collateral damage (meaning many dead males).

SUMMARY OF THE INVENTION

The present embodiments may use a time when adult mosquitoes are still, in order to apply imaging and then pick the wanted insects or zap the unwanted insects. Such a time may be the time when the insect emerges from the pupa, or when the insects are cooled down to a temperature at which they are still. In both cases the insects are still for a period of time which is long enough to be identified by the imaging process and then either picked up or zapped as the imaging process is able to guide a robot arm to find the insect.

According to an aspect of some embodiments of the present invention there is provided a method for mechanical sex-sorting of mosquitoes by extracting a class of mosquitoes from unsorted mosquitoes, the method comprising:
  obtaining said unsorted mosquitoes;
  obtaining images of individuals of said unsorted mosquitoes in a stationary phase;
  electronically classifying said individuals from said images into at least one member of a group of classifications including male mosquitoes, female mosquitoes, and unclassified objects;
  obtaining co-ordinates of individuals of at least one of said male mosquito and female mosquito classifications;
  using a robot arm to reach an individual identified by ones of said obtained coordinates to store or remove said individuals, thereby to provide sex-sorted mosquitoes.

In an embodiment, said classifying comprises using a trained neural network.

In an embodiment, said trained neural network comprises four or more layers.

In an embodiment, said obtaining images comprises obtaining successive frames, generating differences between said successive frames and using said differences to determine which individuals are in said stationary phase.

In an embodiment, said classifying comprises using a recurrent neural network (RNN).

In an embodiment, said unsorted insects are emerging pupae and said stationary phase is emergence.

In an embodiment, said unsorted insects are adults and said stationary phase is obtained by cooling said insects.

The method may comprise tracking movement of individual insects to update respective obtained coordinates prior to using said robot arm.

The method may comprise obtaining said images for classification using a first, relatively high resolution, camera, and carrying out said tracking using a second, relatively low resolution, camera.

In an embodiment, said obtained coordinates are of said male class and said identified individuals are picked off and placed in storage.

In an embodiment, said robot arm comprises a suction device or a blower device to pick off said identified individuals and place in storage.

In an embodiment, said obtained coordinates are of said female class and said identified individuals are destroyed.

In an embodiment, said robot arm comprises a zapper for destroying said identified individuals.

In an embodiment, said zapper is one member of the group comprising an electrode and a laser.

In an embodiment, if an individual is not classified into male or female by a predetermined time, then the image is sent to an operator.

In an embodiment, if an individual is not classified as male by a predetermined time then it is classified as female.

In an embodiment, said insects are cooled in a container having walls, so that the cooled insects stand on an interior side of said walls, the method comprising dismantling said box to present said interior sides of said walls for said obtaining said images.

In an embodiment, said insects are cooled in a container having a trap door and said trap door is opened onto a first moving conveyor, to allow said cooled insects to fall through, said first moving conveyor carrying said insects to an imaging location for said obtaining images, and said conveyor stopping with insects at said imaging location to obtain said coordinates.

In an embodiment, said first moving conveyor is a relatively fast moving conveyor, thereby to prevent piling of insects disrupting imaging, wherein said obtained coordinates are of the female class so that male insects are retained on the conveyor, the first moving conveyor emptying onto a second moving conveyor being a relatively slow moving conveyor, said relatively slow moving conveyor conveying said retained insects for placing in storage cartridges.

According to a second aspect of the present invention there is provided apparatus for mechanical sex-sorting of mosquitoes by extracting a class of mosquitoes from unsorted mosquitoes, the apparatus comprising:
a source of unsorted mosquitoes;
a camera configured to find individual mosquitoes on a stationary phase and obtain images and coordinates of said individuals;
a classifier, configured to electronically classify said individuals from said images into at least one member of a group of classifications including male mosquitoes, female mosquitoes, and unclassified objects;
a robot arm connected to said classifier and configured to reach an individual identified by ones of said obtained coordinates to store or remove said individuals, thereby to provide sex-sorted mosquitoes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the imaging and directing of the robot arms in embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and photographs. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3, 4, 5, 6 and 7 show prototype apparatus for carrying out the method of FIG. 1;

FIG. 17 illustrates a pupa tray with as yet unidentified regions of interest;

FIG. 18 illustrates a region of interest found in FIG. 17 according to the present embodiments;

FIG. 19 shows a track made by an insect in the tray of FIG. 17 and tracked according to the present embodiments;

FIG. 20 shows the effects of piling up on the edges of a tray to prevent classification of individual insects in the pile;

FIGS. 28, 29, 30, 31 and 32 are schematic diagrams showing five different variations or a robot picker according to the present embodiments.

DESCRIPTION OF SPECIFIC EMBODIMENTS OF THE INVENTION

Figure 1:
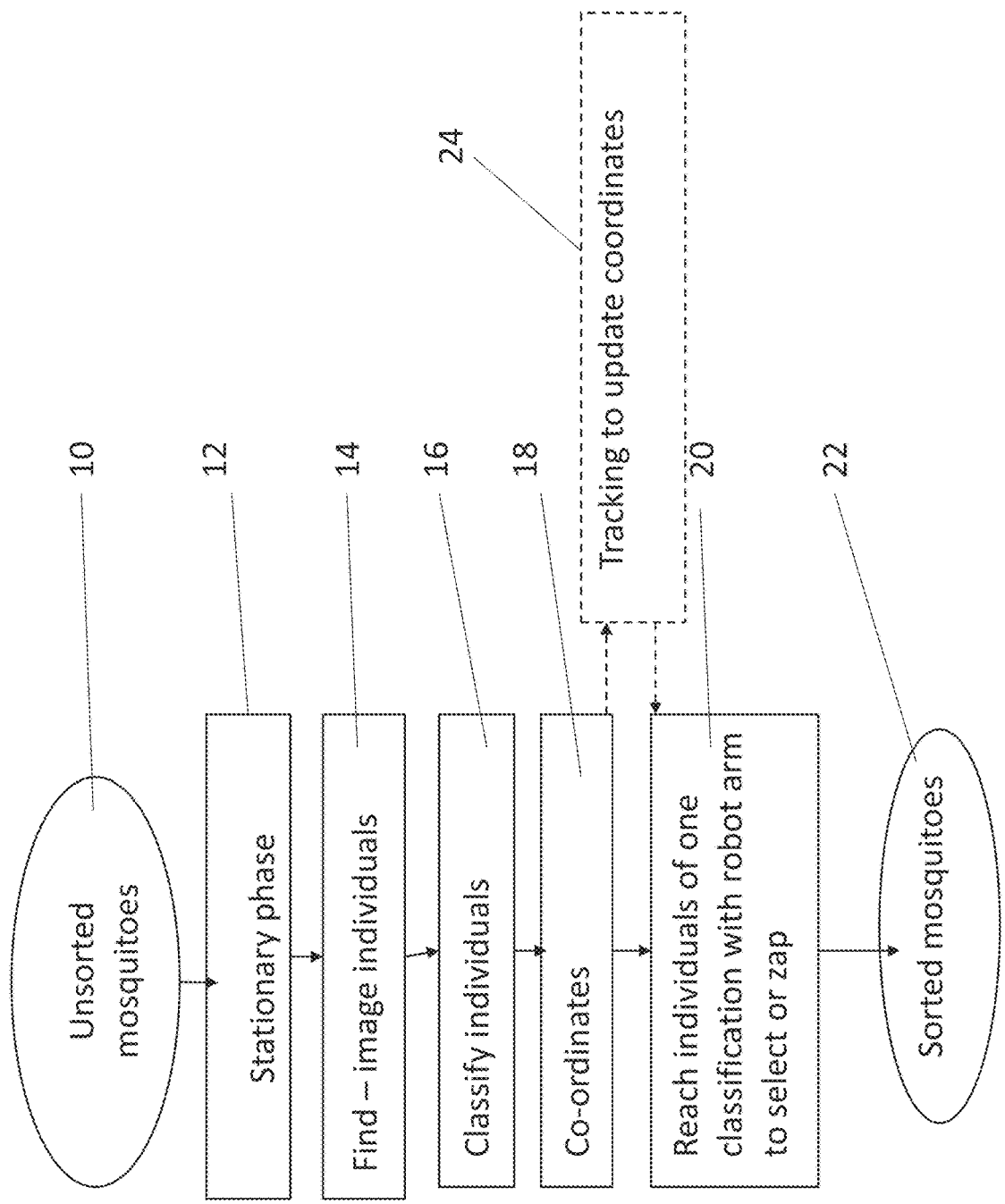
FIG. 1 is a simplified flow chart of a first embodiment of the present invention using a stationary phase to image and classify mosquitoes and then sort accordingly.

The present invention, in some embodiments thereof, relates to sex sorting of mosquitoes and, more particularly, but not exclusively, to a method and apparatus for providing sorted male mosquitoes.

A method and apparatus for mechanical or electro-mechanical or other automatic sex-sorting of mosquitoes by extracting a class of mosquitoes from unsorted mosquitoes comprises obtaining unsorted mosquitoes, obtaining images of individual mosquitoes in a stationary phase, electronically classifying the individuals from the images into male mosquitoes and/or female mosquitoes, and possibly also unclassified objects; obtaining co-ordinates of individuals of at least one of the male mosquito and female mosquito classifications, and using a robot arm to reach an individual identified by the obtained coordinates to store or remove the individuals, thereby to provide sex-sorted mosquitoes.

The stationary phase is any phase in which the mosquito does not move or barely moves. One possibility is when the insects are cooled and remain motionless on walls, or cooled further to fall to the floor. Another possibility is when the adult insects emerge from the pupa.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a flow chart showing a generalized embodiment of the present invention. A method for mechanical sex-sorting of mosquitoes by extracting a class of mosquitoes from unsorted mosquitoes may begin with unsorted mosquitoes 10. A stationary phase is identified, say during emergence as an instar, or applied by cooling 12, and the mosquitoes are imaged in the stationary phase—14. The images are used 16 to classify the individuals. Classes used may include males and anything else, or females and anything else, or males, females and anything else. The coordinates are provided 18 alongside the gender of individuals of interest. In some cases the males are gathered, and in other cases the females are removed.

Then, a robot arm may be used to reach an individual identified by the obtained coordinates to store or remove said individuals, thereby to provide sex-sorted mosquitoes 22.

Classifying may be carried out using a trained neural network, and the neural network may be a classical neural network or a deep network, including a convolutional neural network, or any other kind of neural network.

The trained neural network may comprise four or more layers.

In an embodiment, the stage of obtaining images 14 may relate to obtaining and considering single frames. Alternatively, successive frames may be classified together by generating differences between successive frames and using the differences to determine which individuals are in the stationary phase. Thus if successive frames show a mosquito shape and little change, the implication is that a stationary mosquito is being viewed.

Successive frame classifying may involve using a recurrent neural network (RNN), as will be discussed in greater detail below.

In an embodiment, the unsorted insects are emerging pupae and the stationary phase at 12 is the emergence phase in which the adult emerges from the pupa.

Alternatively, the unsorted insects are adults and the stationary phase is obtained by cooling the insects.

The insects are not necessarily absolutely stationary during the stationary phase, and thus an embodiment uses imaging to track 24 movement of individual insects to update the coordinates obtained in box 18, so that the robot arm moves to the correct location.

Obtaining images for classification may use a first, relatively high resolution, camera, and tracking may use a second, relatively low resolution, camera with a wide field of view. Alternatively a single camera may be used for both, provided that it combines sufficient resolution with sufficient field of view.

In embodiments, the obtained coordinates are of the male class and the identified individuals are picked off and placed in storage. The robot arm may use a suction device or a blower device to pick off the identified individuals and place them in storage.

Alternatively, the obtained coordinates are of the female class and the identified individuals are destroyed or otherwise disposed of. A small number may be retained for breeding. The robot arm may comprise a zapper for destroying the identified individuals, or may as before use a suction device or blower.

The zapper may be an electrode or a solenoid or a laser etc.

In an embodiment, if an individual is not classified into male or female by a predetermined time, then the image is sent to an operator for adjudication. Alternatively, if an individual is not classified as male by a predetermined time then it is classified as female.

In an embodiment, the insects are cooled for imaging in a container having walls, so that the cooled insects stand on an interior side of the walls. Then the box is dismantled to present the interior sides of the walls for imaging.

Figure 2:
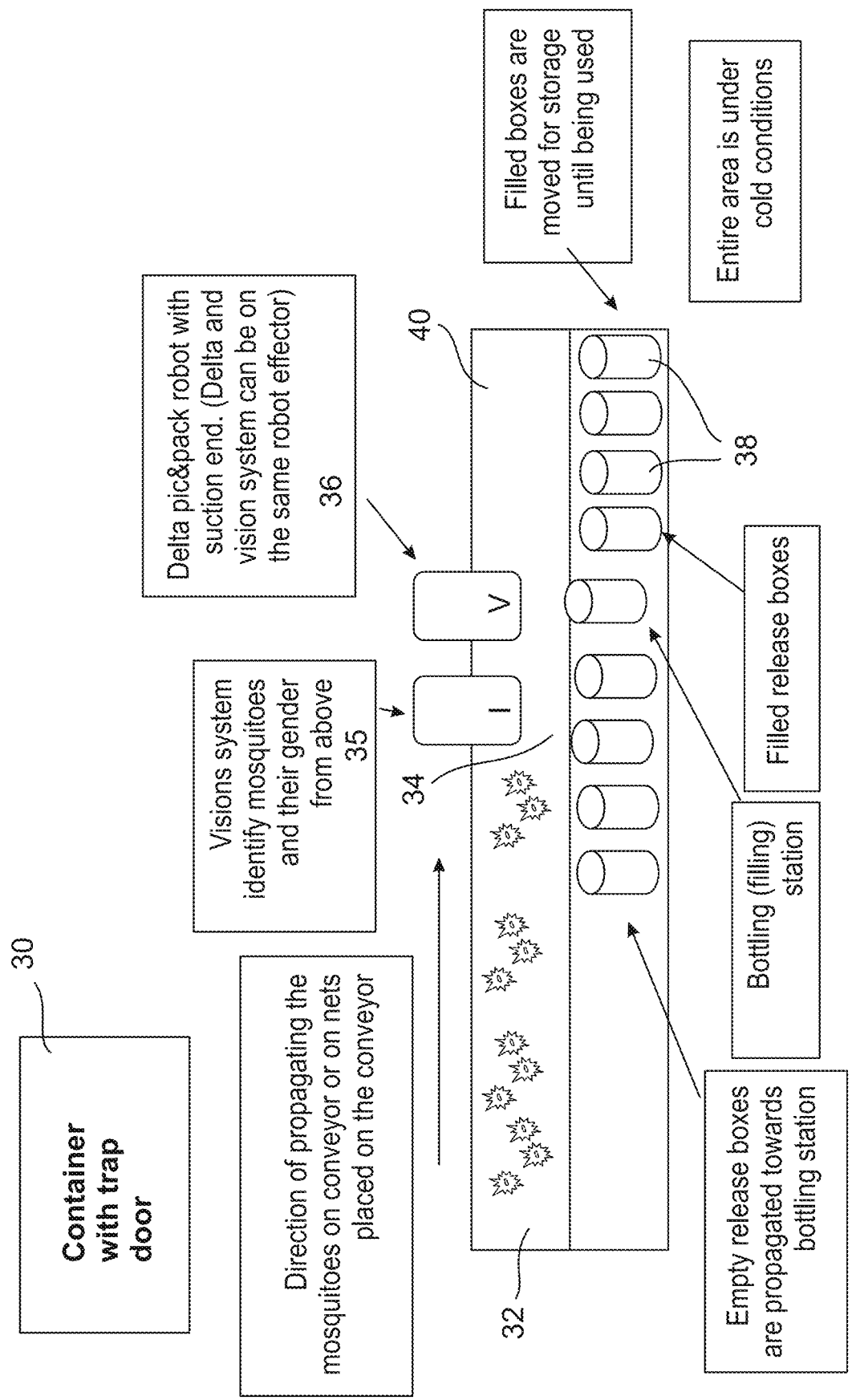
FIG. 2 is a simplified diagram showing an embodiment in which cooled mosquitoes are poured onto a conveyor for imaging in a stationary phase according to FIG. 1.

Referring now to FIG. 2, the insects are cooled in a container 30 having a trap door and the trap door is opened onto a first moving conveyor 32, also held at low temperature, to allow the cooled insects to fall onto the conveyor. The first moving conveyor carries the insects to an imaging location 34 under camera-imaging system 35. The conveyor may stop when insects reach the imaging location to allow for imaging with coordinates, and then robot 36 picks the selected insects, in this case generally the females, leaving the males to fall off the end of the conveyor into release boxes 38.

In an embodiment, the part 40 of conveyor 32 beyond the imaging area may be a second conveyor which collects mosquitoes from the first conveyor and then travels more slowly to the filling area.

The first moving conveyor 32 may be a relatively fast moving conveyor, where the speed spreads out the falling mosquitoes, so that the insects don't pile and disrupt imaging. The first moving conveyor 32 may empty onto second moving conveyor 40, being a relatively slow moving conveyor.

In greater detail, the present embodiments provide technology for automatic or semi-automatic detection and classification of mosquitoes.

In order to be able to perform a good classification and selection of the mosquitos, the identified mosquito needs to be in a position where it can be identified as an individual and seen clearly, and then it should stay relatively still and certainly not fly away between classification and the time at which it can be picked or removed in the sorting process.

Two different embodiments provide these properties in different ways.

A first embodiment uses cooling to cool down the air, so that the mosquitoes do not move and then it makes the classification. In embodiments, the temperature is lowered to ~6-12 degree Celsius, low enough so that the mosquitoes do not fly, but high enough so they continue standing, and not falling on the floor and getting tangled with one another.

A variation of the same embodiment lowers the temperature further, or the cage is shaken with the previous level of cooling, so as knock the mosquitoes down on the floor.

A second embodiment uses a system that monitors a tray of pupae at around the stage of emergence, and utilizes the fact that the mosquito sex can already be visually identified just before the adult mosquito is fully emerged. At this point the mosquito is stationary or almost stationary for several minutes, providing sufficient time to detect, classify and then carry out selection. Such a system is made of a pupa tray with water, pupa and a vision system. As will be discussed, different methods of image classification are suitable for different embodiments, and these include both classical neural networks and convolutional and other networks involving deep learning.

The present embodiments, may automatically sort and handle the adult insects based on the classification process to provide sorted insects in release cartridges.

The present embodiments may either handle the males for selection and further use, leaving the females behind, or handle the females and remove them, leaving the males for further use.

The robotic system may potentially receive a priority list from the detection and classification system, instructing it which mosquito to handle first, as will be described in greater detail below.

An embodiment may include a pupa tray with water and pupa inside.

There may be further provided a vision sensor to detect and classify the mosquitoes upon their emergence.

Optionally a cage with nets surrounding the pupa tray in order to prevent any emerging mosquitoes from escaping to the outside.

A robotic system may contain an arm and a handling tool for handling the individual mosquitoes. The robotic system also includes a controller to receive coordinates and guide the robotic arm and handling tool to move to those coordinates. The movements may be on X-Y-Z axis, providing the ability for the handling tool to reach all areas in front of the surface on which the adult mosquitoes are standing.

In one embodiment, the handling tool may comprise a suction tube and a motor with controller. Suction may be in the order of 3-8 meters per second for a tube diameter in the order of 6-12 mm. Larger tubes are possible but may suck more than just the selected target mosquito, thus upsetting the selection ability of the system.

The handling tool travels to the mosquito X-Y position, and the suction tube is lowered along the Z axis to meet the mosquito.

Reference is now made to FIGS. 3 and 4, which illustrate a prototype in which a pupa tray with water is located below a framework holding a robot arm.

As shown in FIGS. 3 and 4, a proximity sensor 50 may be located above pupa tray 52 to sense the distance to the water surface as a safety measure. The same or another sensor may follow the suction tube 54 which is being operated by robot arm 56 to ensure it reaches a distance of about 0.5 cm from the mosquito, or about 1 cm from the water surface. That is to say the sensor provides feedback on the suction tube position for correct actuation.

Reference is now made to FIG. 6, which is a schematic diagram showing suction tube 62 and motor-controller 64. The tube moves over the area of tray 66. Once the suction tube is above the mosquito coordinates, suction operates to pick off the selected mosquito which travels on to a storage cartridge 58 such as that shown in FIG. 5. The mosquito 60 then enters the cartridge.

In that way, the emerging male mosquitoes are selected and placed into the release cartridges.

For colony maintenance, selected females and males can be transferred and puffed together into rearing cages, to keep the size of the rearing colony. Females can also be eliminated through being transferred into female cages for elimination if needed.

As the mosquitoes are sucked one by one, there may be continuous monitoring of the number of mosquitoes that are loaded into each release cartridge, or into the rearing cages. FIG. 7 illustrates a release cartridge 70 that is full.

In another embodiment, instead of suction of the female mosquitoes, a laser module that can be provided with coordinates, can shoot a laser beam and kill a female mosquito. In that embodiment, the laser beam is directed towards the mosquito female with coordinates provided by the detection and classification process.

The term "zap" is used herein to describe different ways of killing the female mosquitoes, including such use of a laser beam.

In another embodiment, instead of sucking the males, it is possible to wait until they fly.
In that case there are two options:
In the first option, the tray of pupa is placed inside a cage.
The females are extracted or zapped a robotic guided zapper or by a laser beam or other type of zapper, for example an electrode that electrocutes the insects, or a solenoid which, when trigged, pushes the female mosquito into the water to drown.

The males may then be left to emerge into the cage.

By the end of the process the idea is that there is a pupa tray with no pupa, and a cage with males only.

The robotic zapper is either placed inside the cage, requiring a large enough cage, or the zapper can enter through an opening each time the vision sensor classifies a mosquito as a female mosquito.

The vision system is placed at a distance that provides the required resolution for the sensor, be it just above the pupa dish, or above the cage with a transparent roof top and zoom-in capability.

Typical camera resolution may be 5 MegaPixels, that is using a sensor of 2000×2500 pixels. If the field of view is a region having a length of 30 cm, you divide by the dimension and get the number of pixels per mm. The present embodiments may have at least two to three pixels along the length of the distinguishing features of the mosquitoes. The distance of the camera from the tray and the number of pixels on the sensor are thus connected to provide a sensitivity.

Figure 8:
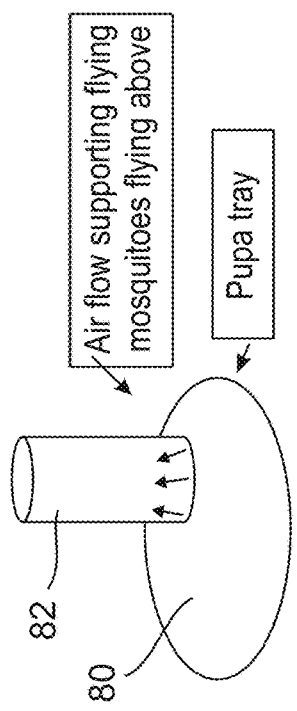
FIGS. 8 and 9 are simplified schematic diagrams showing suction devices for sucking insects into a release cartridge according to embodiments of the present invention.

Reference is now made to FIG. 8, which illustrates a second option. Above the pupa tray 80 there is a tube 82 for guiding the emerging mosquitoes towards release cartridges. In that way, many mosquitoes emerging from a single pupa tray may be guided through ducts towards a release cartridge. Once the system identifies that the number of mosquitoes transferred into that cartridge has reached the required number, the mechanism may be switched to start filling the next cartridge. This can happen for example by moving away the filled cartridge and bringing in below the outlet of the main duct a new release cartridge to be filled.

In order for the cartridges to be actively guided, air flow may be introduced into the duct, to support moving the mosquitoes along the ducts, toward a main duct and then to the release cartridge.

Figure 9:
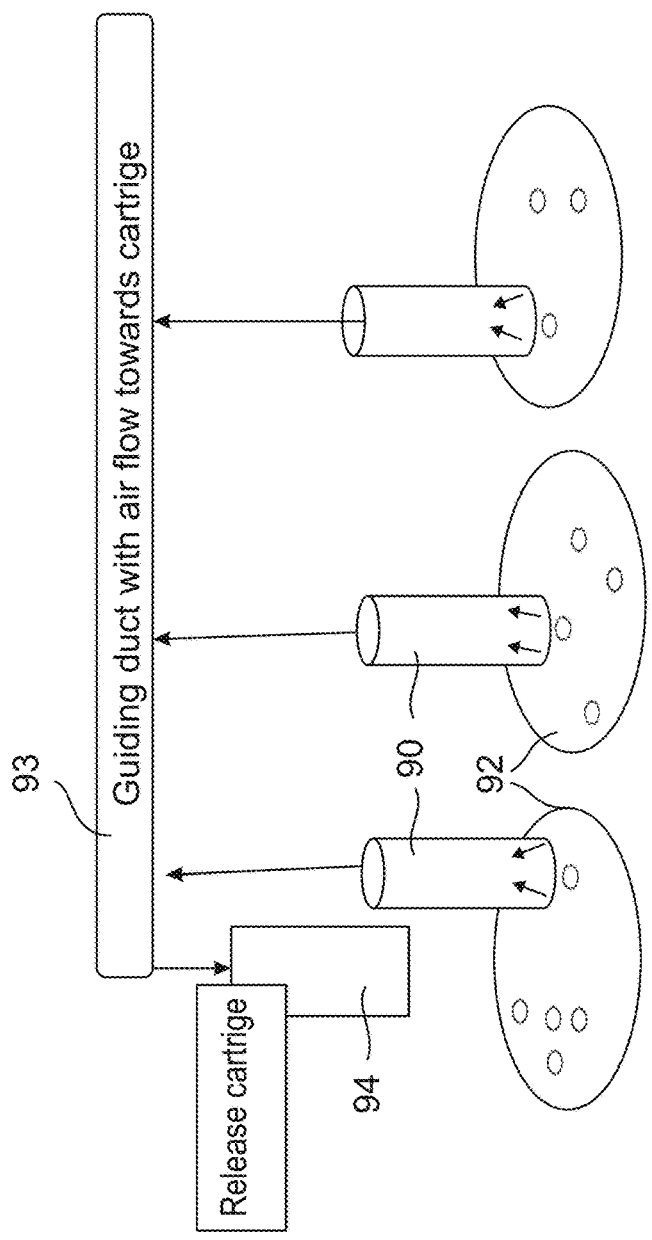

Referring now to FIG. 9, the suction unit 90 may be placed above the correct coordinates of the identified insect in the tray 92 as provided by the camera (not shown) after running the detection and classification process. A guiding duct 93 with airflow leads to release cartridge 94.

The release cartridge 94 has an opening wherein upon pushing from the outside the guiding duct 93 can enter into the release cartridge without letting the mosquitoes escape to the outside.

In prototypes, the emergence process was shown to take about 3-5 minutes, and that after the mosquitoes is fully emerged with all of its 6 legs, it will usually stand still on the water for at least 3 more minutes. Some walked after 3 minutes, some walked or flew after 15 minutes and more.

The detection and classification per each frame was shown to last about 0.5-1.5 seconds, with an average of 1 second.

The distance the robotic zapper needed to move in order to reach the coordinates of the mosquito was in the order of dozens of centimeters. The time required for that is in the order of 2 seconds, including the suction. The classification process may continue in parallel to the robotic operation, hence, while the robotic arm is moving towards a mosquito, the algorithm already classifies the next one, and so the total cycle between mosquitoes is 2 seconds. This means that over 24 hours, a robot can sort around 43,000 mosquitoes. It may be decided to use fresh plates every 24 hours to increase productivity. Hence for a daily sorting production rate of 5M mosquitoes (or 35M per week), some 116 robotic systems are needed.

Today, the cost of a single robot at that size and reach is in the order of 5,000 Euro, resulting in a total cost of around 500K euro for the automatic sorting equipment for a facility with a production rate of 35 millions mosquitoes per week. This is much more affordable than the hundreds of personal that would be required in order to achieve the same rate manually.

In the second main embodiment as presented in the beginning the system includes a cooling unit, able to lower the temperature to 6-12 Celsius with 1 degree Celsius resolution, a cage with unsorted adult mosquitoes, a robotic system comprising a zapper and a mechanism for travelling along the sides and top-bottom of the mosquito cage, preferably from the external side of the cage.

The method comprises cooling the temperature and waiting five minutes until the mosquitoes have ceased flying but are rather resting on the cage walls.

Detection and classification is carried out on the mosquitoes, and for individual mosquitoes, the gender is output. If the robot is needed because the classification indicates a mosquito that needs to be collected or zapped, then an output is provided giving the coordinates on the walls and gender.

The vision sensor, typically a camera, is placed alongside the cage to cover all walls. Alternatively, multiple cameras may be used.

Once a female mosquito is classified, a laser beam kills the mosquito at the female mosquito coordinates, or alternatively, a suction tube is brought to the coordinates to suck the female mosquito through the net. The suction in that case would be higher than in the previous embodiment where the targets are the adults emerging from the pupa stage. A typical speed may be in the range of 20 m/s in order to be able to get over the mosquito's efforts to cling to the cage walls. In another embodiment the suction unit zapper may be placed inside the cage.

Figure 11:
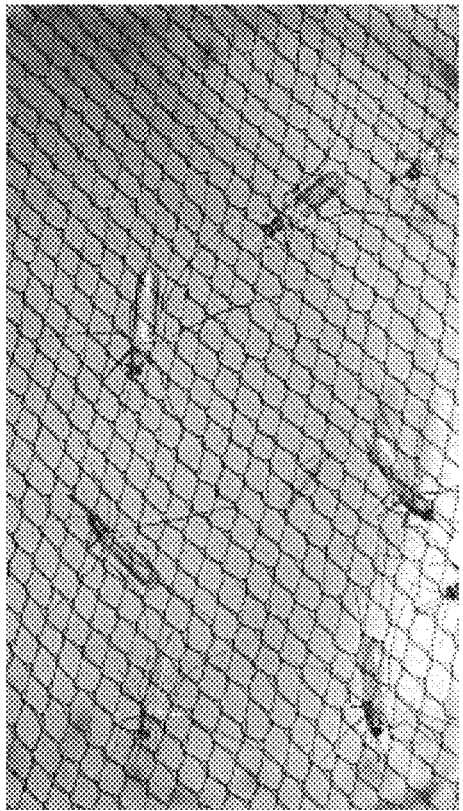
FIGS. 10 and 11 show cooled insects on cage walls, in a state ready for imaging and classification according to embodiments of the present invention.
Figure 10:
Figure 12:
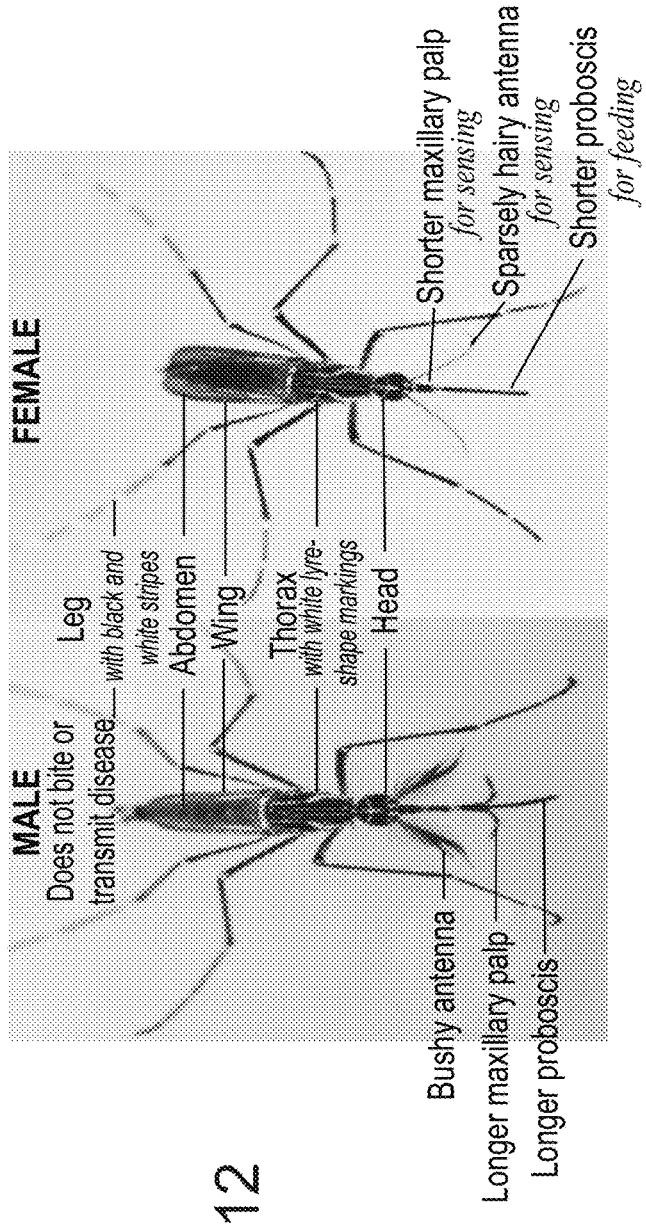
FIG. 12 is a chart showing the visual differences between male and female mosquitoes.

Referring now to FIGS. 10 and 11, the mosquitoes 100 are in enclosures 102 which are cooled to around 8 degrees. The mosquitoes appear clinging to the box wall after the temperature is lowered. Distinct gender features can be easily seen and mosquitoes can be classified. FIG. 12 shows male and female mosquitoes side by side and shows the visual differences between the two. Specifically, in the male the antenna is bushy, the maxillary palp is longer and the proboscis is also longer. In the female the antenna is smooth, and the maxillary palp and proboscis are both shorter.

The following relates to a method of automatically detecting and classifying mosquitoes as males and females, and is described in the case of emergence from a pupa, but also applies to imaging under cold conditions.

For a semi-automatic version, the system may signal an operator on its finding for a decision.

As well as a classification, the system may provide the coordinates of the classified mosquito to the robotic controller to work according to any of the options mentioned herein, such as to guide a suction tube and suck the mosquito to transfer it to a cartridge, kill it with laser beam, etc.

The concept is primarily for mosquitoes but may apply to other applications in which insect rearing is involved, sex sorting is required and there is a distinguished visible patterns that can be the target of computer vision algorithms in a similar way to the methods suggested in this application.

In the following we describe the present embodiments with reference to the version in which the mosquitoes are emerging, but the same details apply mutatis mutandis to lowering the temperature.

The same algorithm and method apply to detecting and classifying under cold conditions, but there are differences. In cold conditions [1] There is no emergence process that has to be captured, [2] there is no prioritization, since there is no emergence, [3] the background has less visual noise (the pupa shell, the water surface), which improves the general performance (speed to reach a positive result).

When the mosquito orientation is such as in FIG. 12, those features are easily noticeable as long as there is a line of sight between the mosquito and a direct vision sensor located above.

As suggested, achieving this can be when either the temperature is low, the mosquitoes cling to the walls or, during the emergence process.

The emergence process takes a few minutes (around 3-5 minutes with possible exceptions) until the mosquito emerges out of its pupa, and then it may continue standing on the water. That is to say the emerging mosquito may walk slightly but usually not much. Generally the emerging mosquito remains still for an additional few more minutes to harden and dry its exoskeleton. During all that time, as it almost does not move, its orientation is the same with reference to a vision system observing it from above.

Figure 14:
FIGS. 13 and 14 illustrate two actual images taken from a pupa tray with emerging adults for classification using the embodiments of the present invention.
Figure 13:

FIGS. 13 and 14 are actual images of insects emerging from pupae in a tray full of pupae.

FIG. 13 shows a male and FIG. 14 shows a female.

The outputs are the coordinates of the classified mosquitoes, provided for the operator or a robot controller.

The system may comprise a tray of pupae. As in the second embodiment described above, there is a cooling unit for cooling down to 6-12 degree Celsius, and there may also be provided a surface for knocked down mosquitoes.

A vision system such as a camera, controller unit and software, may acquire a sequence of continuous frames of the mosquito in order to detect classify and/or track its position.

Since the mosquito can be oriented in different ways, with some visual noise in the background, embodiments may use a deep learning approach based on convolutional neural networks to detect and classify the mosquito sex.

In another embodiment, pre-processing of the image may be carried out using methods from classical image processing, such as obtaining outlines etc. Then the deep learning is provided with the processed results.

The vision module may processes each of a plurality of frames taken separately and independently. Alternatively the succeeding frames can be used together to make available a sequential form of the problem, and treat the input as a video. However it is generally believed that for video processing, wrapping a single image processing module in a RNN architecture may gain better results.

The present embodiments may contain one or two cameras above the tray of pupas in which tray it is expected that the adults are about to emerge any moment, A robot arm with a laser, or any other zapper may also be provided that may operate at the given mosquito coordinates according to a set of algorithms.

The set of algorithms may find where, in the image and in the physical world, there is an emergence of a mosquito from a pupa and may then track its location with time.

A high resolution camera, may look for the features of the mosquito that particularly identify the gender, such as the antenna area. In addition there may be a low resolution camera that is required for tracking. Alternatively, a single camera may provide both detection-classification and tracking, if the tracking area is covered within the camera field of view (FOV).

The inputs for imaging and location are: a continuous sequence of images from an upper projection of a tray with mosquitoes and pupae in water inside the tray.

A requirement may be:

"Finding the real world coordinates of all female mosquitoes in the captured tray at any given moment".

In that case the object will be classified either as female, or "other" (either male or pupa or other visual noise). This can be useful for quality control or when it is only needed to extract the females. It is possible to use the algorithm breakdown below and define a different purpose—"Finding the real world coordinates of all male mosquitoes in the captured tray at any given moment", or further to "find the real world coordinates of all male mosquitoes and female mosquitoes in the captured tray at any given moment".

Figure 15:
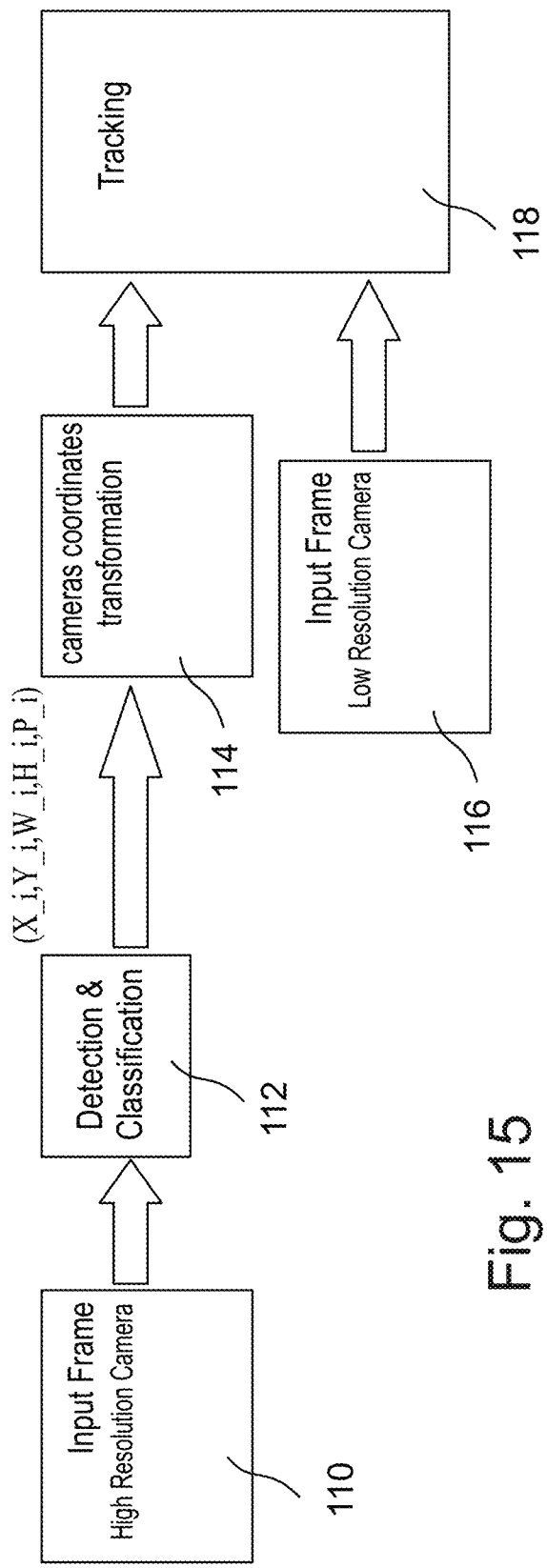
FIG. 15 is a simplified flow chart showing a process for obtaining high and low resolution frames and carrying out detection, classification and tracking.

For that purpose, we may use the following features:
1) Camera calibration (one time for system set-up, and as necessary during maintenance etc.)
2) Detect ROI's (region of interest) of each mosquito.
3) Classify gender of each mosquito
4) Prioritize mosquitoes
5) Track each classified female mosquito
6) Transform pixel coordinates system into real-world coordinates system Reference is now made to FIG. 15 which is a block diagram describing the imaging and location flow, with the assumption that two cameras are used; one for detection-classification (aka High Resolution Camera) and the other with larger FOV for tracking (aka Low Resolution Camera).

In box 110 a high resolution frame is obtained. In box 112, detection and classification is carried out. In box 114, coordinates are taken and transformed for the camera and robot frames of reference. In box 116 a low resolution frame is obtained, and in box 118 tracking is carried out to update the coordinates.

The layout can be duplicated to match a layout with more trays or camera. Tracking can be mutual to a few camera looking each on part of a tray.

Upon system set-up there is a camera calibration procedure in order to enable finding the transformation between the pixel's coordinates system and the physical coordinate system.

If the system consists of two cameras, e.g. high & low resolution as suggested above, then a calibration between each camera may be derived from the calibration parameters of each camera.

Camera calibration using a check-board or other patterns is known, and such known methods are provided as an example:

"A Flexible New Technique for Camera Calibration", Zhengyou Zhang, 1998, Microsoft (www(dot)microsoft (dot)com/en-us/research/publication/a-flexible-new-technique-for-camera-calibration/).

"A Four-step Camera Calibration Procedure with Implicit Image Correction", Janne Heikkila and Olli Silvén, University of Oulu, Finland.

The implementation of the algorithm is common knowledge, and sample code is publicly available.

In camera calibration there is a model that is divided into extrinsic (orientation and location) and intrinsic (mainly optical) parameters. Having all of these parameters allows a transformation between the image coordinates system and the real-world coordinate system.

Calibration is done by capturing several pictures in various orientations of a checkerboard or other easy to detect pattern. By corresponding detection or marker points in each of the pictures, an optimization process may be converted to the correct camera model parameters.

Once we have the transformation parameters (intrinsic and extrinsic parameters) we can translate mosquito location to a physical location for the mechanical system to work.

Since the cameras are mechanically stable, the calibration process is done once (or for maintenance reasons every couple of months\years).

With two cameras, and having the transformation parameters for each camera we calculate the transformation between the two cameras' pixel coordinate systems. Then we can use coordinates from the high resolution camera and transform them into the low resolution camera for the tracking algorithm, and output them either for the mechanical zapper or pinpointing for a human operator where the classified mosquito is to be found.

An accuracy of the calibration is a system parameter that is used for the tracking algorithm and for the mechanical cannon.

The detection (the task of finding where the mosquitoes are in the image) and the classification (the task of determining which gender it is) may be jointly solved by any of the following algorithms as examples:
Single Shot MultiBox Detector (https://arxiv(dot)org/abs/1512[[ ]](dot)02325 Authors: Wei Liu 1, Dragomir Anguelov2, Dumitru Erhan3, Christian Szegedy3, Scott Reed4, Cheng-Yang Fu1, Alexander C. Berg1, UNC Chapel Hill 2Zoox Inc. 3Google Inc. 4University of Michigan, Ann-Arbor).

Faster rcnn: www(dot)arxiv(dot)org/abs/1506[[ ]](dot)01497 ("Faster R-CNN: Towards Real-Time Object Detection with Region Proposal Networks", authors: Shaoqing Ren, Kaiming He, Ross Girshick, and Jian Sun).

Yolo: www(dot)pjreddie(dot)com/media/files/papers/yolo (dot)pdf.

These kinds of algorithms may train a network that is a combination of an RPN (region proposal network) and a classification network that shares the same convolutional features. The RPN proposes various bounding boxes that contain an object with high probability and this way actually tells the classification network where to look in the image. The classification network may be trained to determine to which class the object belongs.

In the present embodiments, concerning detection-classification of mosquitoes, we may define the possible classes as male\female\none or only as female\none or only as male\none In order to train the network we may collect a large number of labeled pictures containing male and female mosquitos.

To train for only one class, female for example, we may provide the network with either male pictures or background pictures for the non-female class. This way the network may train to look for the relevant attributes of females and not general attributes of mosquitos that are common to males and females.

The background pictures may be empty water or pupas or mosquitoes whose gender cannot be determined yet.

The classification net in each of these algorithms may be changed and we may use transfer learning as fine tuning or as a feature vector, which may be done using nets such as Alexnet, VGG and Inception.

Transfer learning is described in those examples: "ImageNet Classification with Deep Convolutional Neural Networks", Alex Krizhevsky, Ilya Sutskever, Geoffrey E. Hinton (www(dot)papers(dot)nips(dot)cc/paper/4824-imagenet-classification-with-deep-convolutional-neural-networks(dot)pdf). "VERY DEEP CONVOLUTIONAL NETWORKS FOR LARGE-SCALE IMAGE RECOGNITION" Karen Simonyan & Andrew Zisserman (www(dot)arxiv(dot)org/pdf/1409[[ ]](dot)1556v6(dot)pdf).

The output of the detection & classification for a single image is a list of rectangles (ROI's) and corresponding probabilities as to whether each of them is a female mosquito, or a general probability that the object belong to each of the classes. This output is a list of vectors $(X\_i, Y\_i, W\_i, H\_i, [P\_i\_1, \ldots P\_i\_n])$ where: I is ROI detected index and n is the number of classes:
- $(X\_i, Y\_i)$=are coordinates in the image of where the detected ROI is
- $(W\_i, H\_i)$=are the width and height of the detected ROI, and
- $(P\_i\_1, P\_i\_2, \ldots P\_i\_n)$ is the list of probabilities of the object in the ROI to belong to each of the classes.

Figure 16:
FIG. 16 is a view of a pupa tray with classification events according to embodiments of the present invention.

Reference is now made to FIG. 16, which shows a tray of pupae and emerging adults. Results are shown of a detection & classification algorithm for two classes and 5 detected insects. It is to be noted that each class is given a probability.

A possible network configuration may be an RNN (recurrent neural network) which is a network that store state and classify differently according to its current state.

The architecture we propose works on a single image. It is known that in video processing there is an advantage to using RNN architecture. In this way the continuity of the images taken before the mosquito fully appears affects the probability that it will be male or female. The accumulated additional knowledge from each frame increases the probability for positive classification.

Relevant methods:
www(dot)cv-foundation(dot)org/openaccess/content_cvpr_2015/papers/Ng_Beyond_Short_Snippets_2015_CVPR_paper(dot)pdf.
www(dot)static(dot)googleusercontent(dot)com/media/research[[ ]](dot)google(dot)com/en//pubs/archive/42455(dot)pdf.

A further implementation also uses previous frames to process a current frame and thus comes under the heading of using video as input.

In this implementation, since the camera is stable, and the pupas hardly moving, only areas of emergence change over adjacent frames. Thus we are able to detect the moment of emergence to be utilized for prioritization as will be discussed in greater detail below. Such knowledge can be used by adding a term to the loss function of the RPN that describes a delta between successive image frames, thus the L2 measure of images or of feature space. In other words the embodiment punishes results of detection where there is little variation and incentivize the RPN for detection results where there is high variation.

During the emergence phase there arises a point in time when the mosquito stops changing its form, which point may be confirmed against an average or maximum time from beginning to end of emergence, or from the moment either six legs of the mosquitoes are out of the pupa.

One method is to determine the time that the image ROI begins to change more rapidly, say using a threshold on adjacent image L2 deltas. The approach is feasible since the pupa images before the emergence process begins are stable, older pupa reaching the stage of emergence hardly move in water. The pupa trays may already be sorted and tagged according to date of pupation (transformation from larva to pupa).

A second method is to train the classification network to classify between more than two classes, namely male and female, and instead use four or more classes: young male, adult male, young female, and adult female. The young male or female classes are defined as those mosquitoes whose legs are not yet fully seen and adult males or females are those mosquitoes whose body is fully exposed. Using this method the number of classes can be extended to more than four for a finer distinguishing of different levels of emergence.

The system may store in memory all instances of emerged mosquitoes and their timing (according to above rule), and then provide the next mosquito to be handled according to a FIFO queue (first to emerge, first to be handled).

The training process of the neural networks is a process that may be carried out once using a large labeled database. There are many factors that affect good training: selecting activation functions, selecting optimization model, how to initialize the weights of the net, determine hyper-parameters, dropout, data augmentation and many more.

The result of a good training process is a set of final values of the weights of the neural networks, which can then be used to classify the images.

Using a trained network on the training database may give the time since the start of emergence that is required to arrive at a successful classification.

For example, the average number of frames (given a constant frame rate) from the start of emergence until the gender classification may be known with 90% probability to be 250 frames (at a rate of 2 frames per second). This information, which may be collected during the training process, may serve the robotic system afterwards to know how much time remains to operate on the classified mosquito.

FIG. 17 is a typical input image where lots of pupae are seen and a region of interest needs to be looked for.

FIG. 18 show a region of interest that has been found in FIG. 17 and contains an adult mosquito needing classification.

Tracking may be carried out using a lower resolution camera, if provided.

Once fully emerged, a mosquito may travel on the surface and tracking is suggested to provide correct coordinates for the operator/robotic handling tool.

Tracking algorithms exploit information of a movement model that contains common velocities and accelerations, to punish\incentivize possible locations of the target in the next frame. Using tracking, partial occlusion or error on the target detection can be compensated.

Tracking parameters for the tracking algorithm may include:

Average/maximal velocity of mosquitos;
Average/maximal acceleration of mosquitoes;
Average/maximal of movement duration;
Angular velocity of movement;
Angular acceleration of movement;
Camera parameters, such as focal length, distance of camera from tray, camera orientation) for translate all spatial units to pixel units; and
Camera exposure time to avoid blurring of a moving object.

An existing tracking algorithms that may be used is a Kalman filter based tracking algorithm.

FIG. 19 shows an insect 117 and a track 119 that the insect 117 has followed.

A pupa tray such as in FIGS. 17 to 19, contains pupae and water. A vision sensor may capture frames from the tray and a deep learning algorithm uses the frame to detect-classify an emerging mosquito. Then the tracking algorithm tracks the mosquito if it moves. Then optionally the coordinates may be sent to an operator in the semi-automatic process, or tracked coordinates may be sent to a robotic system to carry out suction of the mosquito or killing the mosquito with a laser beam or other means.

An alternative embodiment may work on insects as they are warmed and slowly become active. The embodiment may involve cooling of the air where the mosquitoes are stored to a temperature of 6-12 degrees, so that the mosquitoes are resting, almost not moving, but not falling on the ground. Alternatively, the temperature may be set to lower than 6 degrees, so that the mosquitoes are motionless on the floor.

The vision sensor then operates on the cage or plate with the cold and motionless mosquitoes. As in the previous embodiment, a vision algorithm which may be based on deep learning may detect-classify the mosquitoes. If the temperature is above six degrees then tracking may be needed as the mosquitoes do move somewhat. At temperatures below six degrees there is no motion and tracking is not needed.

If training only one class (female for example) one may provide the network either male pictures or background pictures to the non-female class. This way the network may train to look for the relevant attributes of females and not general attributes of mosquitos that are common to males and females. This may create a more efficient network.

An embodiment may run two networks in parallel on the same frames—one that classifies only females, and a second that classifies only males.

As mentioned above, instead of working on individual frames, using video may have an advantage.

If using video then a possible network configuration is RNN (recurrent neural network) which is a network that stores a state and classifies differently according to its current state. The continuity of the images taken before the mosquito fully appears affects the probability that it will be male or female. The accumulated additional knowledge from each frame increases the probability for positive classification.

The system may be able to identify, that is detect the emerging mosquito and where it lies in the emergence process, that is the system may identify the point in time when a mosquito is first fully emerged. Metrics that may be used include average time from start of emergence. Alternatively visual classification of parts of the emergence process may be used. The results are used to enter the current emerging mosquito into a queue for the robotic system, which the robotic system may then deal with in order.

For scaling the detecting and sorting process to large quantities, an automated system may continuously feed the vision system with mosquitoes, however the mosquitoes should be in a state in which they can be clearly imaged. Thus the mosquitoes should be separated from each other, or at least not one on top of the other, so that vision system is able to identify the unique gender features of individual mosquitoes and provide an answer as to whether the object is a mosquito and then if it is a male or female mosquito.

However, in order to increase the yield of the system, large numbers of mosquitoes may pass through the vision system per unit time.

However, if one takes a storage compartment with a large number of mosquitoes and simply decreases the temperature until the mosquitoes fall motionless, then one simply forms piles of indistinguishable individuals. FIG. 20 shows a plate of Asian Tiger mosquitoes, where the temperature is reduced below 8 degree Celsius and the mosquitoes have formed piles in which individuals cannot be classified.

Here we easily notice a situation in which for the middle area 122, where mosquitoes are not one on top of the other, it is easy to identify the mosquitoes, and also their sex, however at the edges, exemplified by 120, we see bundles of mosquitoes for which it is not possible to identify the single mosquitoes and their sex.

In the following we provide two embodiments for a continuous feed of mosquitoes without piling one on top of the other.

A first embodiment comprises:
a. A cooling system;
b. Mosquito storage compartments;
c. Conveyance mechanism to move mosquitoes forward;
d. Vision system with controller. The controller may be connected to the conveyor to stop when required and to provide coordinates;

e. Pick and place robot to suck or blow. For example it may include a common suction pipette or electric air pump or a blower which can be used either for blowing or in reverse as a suction device. The robot may puff male or female mosquitoes. Alternatively a zapper such as a laser beam may puncture or extract female mosquitoes in any other way which kills them.

In the embodiment the temperature is lowered so that the mosquitoes fall onto the floor below. However the floor is moving, since the floor is a moving conveyor, and thus no piling up occurs.

Figure 21:
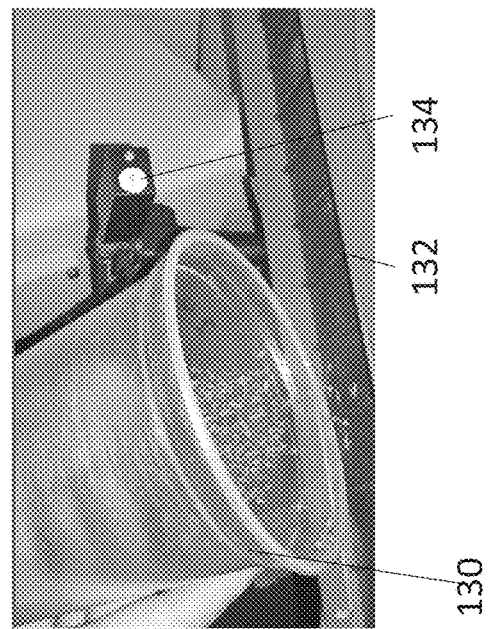

FIG. 21 illustrates mosquitoes being dropped from container 130 onto a moving conveyer 132, where the motion of the conveyor is used to ensure mosquitoes are spread out and not piled up. On the right side is a sensor 134 to identify the mosquitoes from above.

Figure 23:
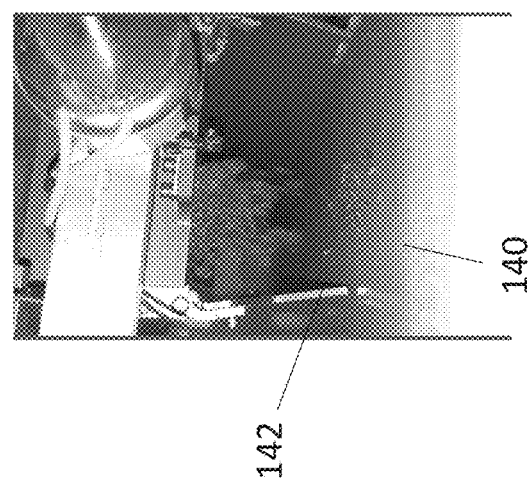
FIGS. 21, 22 and 23 illustrate pouring of cold insects onto a conveyor for classification without piling according to embodiments of the present invention.
Figure 22:
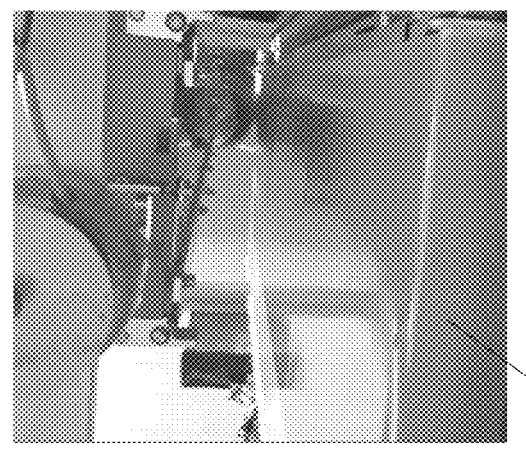

A variation is to cool the mosquitoes so that they fall in a pile, and then open a trap door underneath onto a moving conveyor. This is shown in FIGS. 22 and 23. FIG. 22 shows belt 140 without any mosquitoes and FIG. 23 shows the belt with mosquitoes falling on after trap door 142 has been opened.

In FIG. 23 the storage trap doors are opened, and mosquitoes fall while the conveyor is moving, and as seen, mosquitoes are separated on the conveyor.

Figure 24:
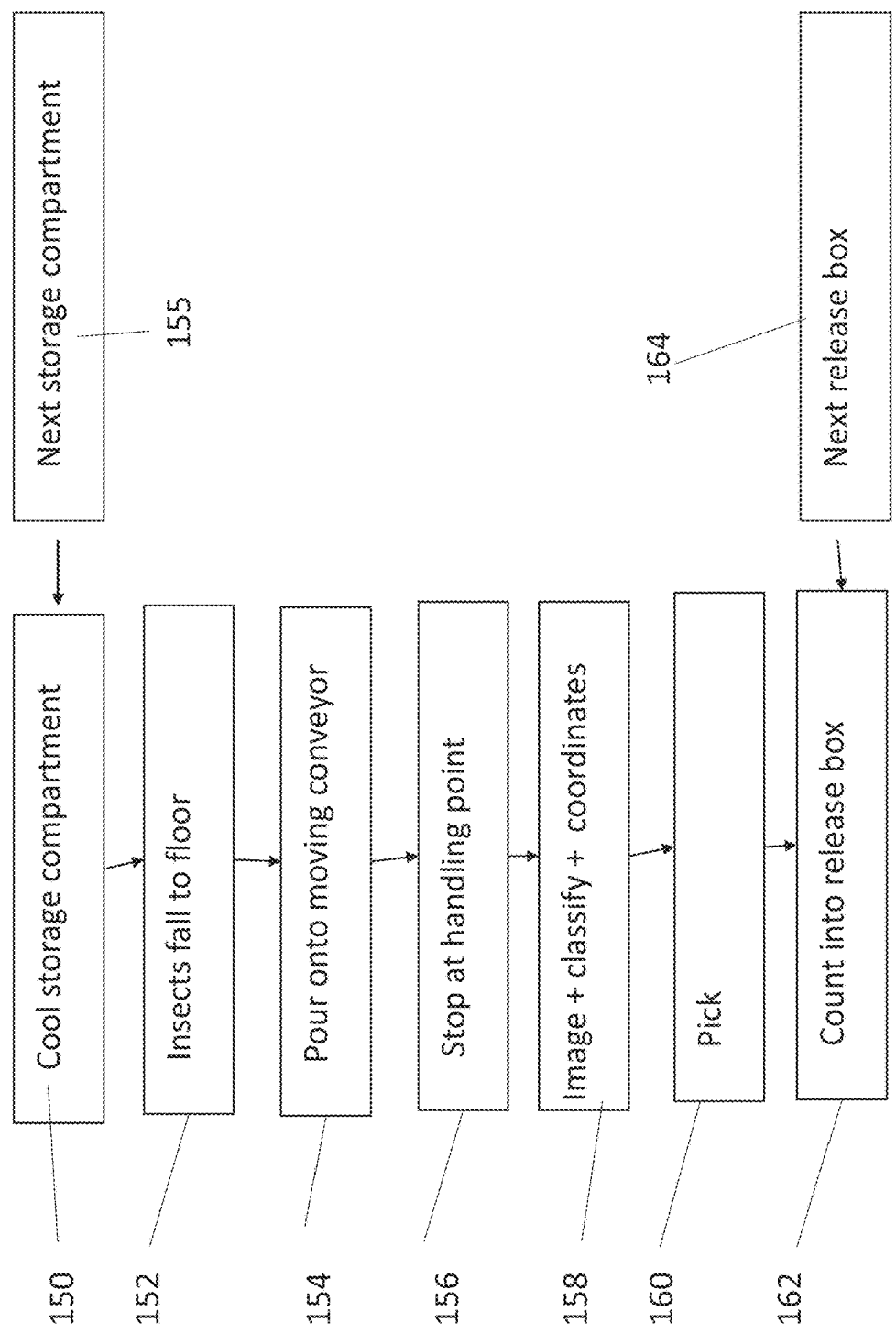
FIG. 24 is a simplified flow chart showing a procedure for pouring insects onto a cold conveyor and classifying according to embodiments of the present invention.

A procedure is shown in the flow chart of FIG. 24.

a. Mosquito storage compartments are held at a low temperature as mentioned above—150.
b. Mosquitoes inside the storage compartments are now knocked down—152.
c. Mosquitoes may then be transferred to the conveyor—154, by pouring them directly on the conveyor. Transfer may be carried out while the conveyor is moving in order to ensure separation. Transfer happens by pouring the mosquitoes directly from the storage or using another item to transfer them from the storage to the conveyor. For example a suction tube may suck the mosquitoes from the storage floor onto the conveyor surface.
d. Once most or all of the content of a storage compartment is transferred onto the conveyor, another storage compartment (or set of compartments, in order to work in parallel) 155 is brought in such proximity to the conveyor to repeat the process.

2. The conveyor may move the mosquitoes under cold conditions as mentioned above towards a robotic handling point. In embodiments, two conveyors may be used. In such a case, the first conveyor may have been used to separate the mosquitoes, and at the end of the first conveyor the mosquitoes may then fall onto the main conveyor that brings the mosquitoes to the robotic inspection and sorting station. In such an example, the two different conveyors may also move at different speeds. A higher speed may be useful to separate the mosquitoes, which then fall onto the secondary conveyor, to move slowly towards the robotic station.

3. At an inspection point, a top camera detects and classifies the mosquitoes according to sex 158 as explained above. The conveyor controller may command the conveyor to stop moving 156 for a short period, say a few seconds, until the vision system algorithm completes the detection-classification process for the objects in the field of view. The conveyor moves again, and once the field of view is again full with as yet unclassified mosquitoes, the conveyor stops again. Alternatively, the detection-classification process may happen at the same position at which the picking robot is located as will be described below. In this alternative, the conveyor stops, the picking robot picks the classified mosquitoes, and then the conveyor moves again a pre-defined distance to enable another set of mosquitoes to be located both under the vision and the picking robot reaching area.

4. Receiving the coordinates and performing tracking of the mosquitoes may be carried out by one or two cameras.

5. A picking robot, for example a delta pick and place robot, receives the coordinates of the mosquito picks 160. Picking may be as follows:
   a. The picking robot holds a suction source;
   b. The suction source sucks the mosquitoes approaching from the conveyor;
      i. either into a temporary suction tube, which are then expelled into a release storage unit or cartridge when full, that is when they receive a pre-defined number of sucked mosquitoes;
      ii. Or after each suction the mosquito is expelled directly into a release storage unit that is located close to the suction robot, preferably also under cold conditions.
   c. The robot may count 162 the number of mosquitoes sucked and expelled into release boxes;
   d. Once the release storage unit has reached a certain number of mosquitoes the release storage box is exchanged for a new one 164.

The change may be manual or automatic.

Figure 25:
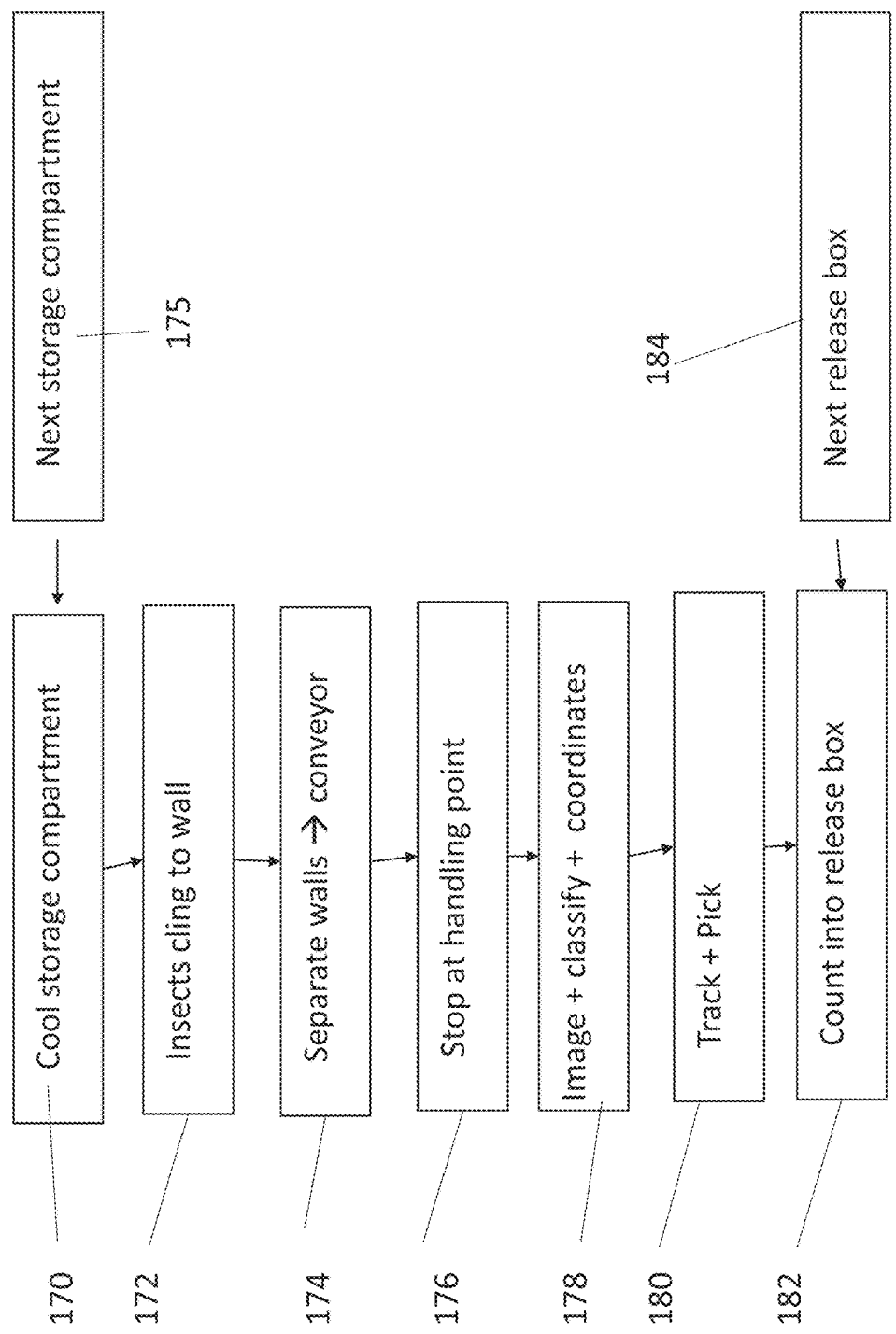
FIG. 25 is a simplified flow chart showing an alternative procedure for placing container walls with standing insects onto a cold conveyor and classifying according to embodiments of the present invention.

A second embodiment comprises
a. A cooling system; and
b. Mosquito storage compartments having walls to which mosquitoes may cling. The storage compartments may be de-attached or folded out, so that instead of a box, after de-attaching the walls from each other, the result is a set of panels to which the mosquitoes cling. The walls may comprise aluminum nets with small holes. The mosquitoes may thus be presented resting on nets without flying, and not being one on top of the other.
c. A conveyor or rail system may move the panels with mosquitoes forward;
d. Vision system with controller as discussed above. The controller may be connected to the conveyor to stop the conveyor when required so as to provide the pick and place robot as discussed above with the necessary coordinates;
e. The pick and place robot as discussed hereinabove The procedure is now discussed with reference to FIG. 25 which is a flow chart illustrating the present embodiment.

Initially the temperature is lowered 170 using the cooling system so that the mosquitoes do not fly in the storage compartment, and also do not falling onto the storage floor. Such a temperature for the Asian tiger mosquito is for example usually below 13 degrees Celsius not flying, but higher than 4 degrees Celsius allowing the insects to cling to the walls—172. A preferred temperature is above 8 degree Celsius.

The cage walls on which the mosquitoes are resting are then taken out 174 and attached to the moving conveyor or rail system.

The cage walls when placed on the moving element (conveyor or rail), are oriented so that the mosquitoes are resting on the top part which was previously the internal part of the storage compartment, and the vision system and also the pick and place robot unit may thus have direct access to the mosquitoes.

The conveyor may propagate the walls forward, and with them, the mosquitoes, under cold conditions as mentioned above towards the robot handling point.

At the robotic handling point, a top camera detects and classifies mosquito sex—178, as discussed hereinabove. Tracking may be required since the temperature is high enough to allow mosquitoes to walk on the walls. The conveyor controller may command the conveyor to stop moving for a short period 176, say a few seconds, until the vision system algorithm has completed the detection-classification process for the objects in the field of view. Afterwards the conveyor may move again, and once the field of view is again full of unclassified mosquitoes the conveyor may stop again. Alternatively, the detection-classification process may take place at the position where the picking robot is located, and thus the conveyor may wait for the picking robot to pick the mosquitoes of the appropriate class 180, and afterwards move a pre-defined distance to enable another set of mosquitoes to be located both under the vision and the picking robot reach area.

The various embodiments for picking the mosquitoes are the same as in previous embodiments and are not repeated.

If the mosquitoes are already sorted so that there is only one sex inside the cages, then the embodiments may load the release boxes with a pre-determined number of mosquitoes. The vision system in such a case will only need to detect and classify a single class of mosquito, without the need to classify it further as a male or female. The robot may then pick and place the mosquitoes using suction into the release boxes as described above.

In embodiments, if the vision system is unable to classify the mosquito as a female or male, it may send the image to an operator, who may carry out the classification. Other embodiments may zap unidentified mosquitoes along with the females.

Figures 26, 27:
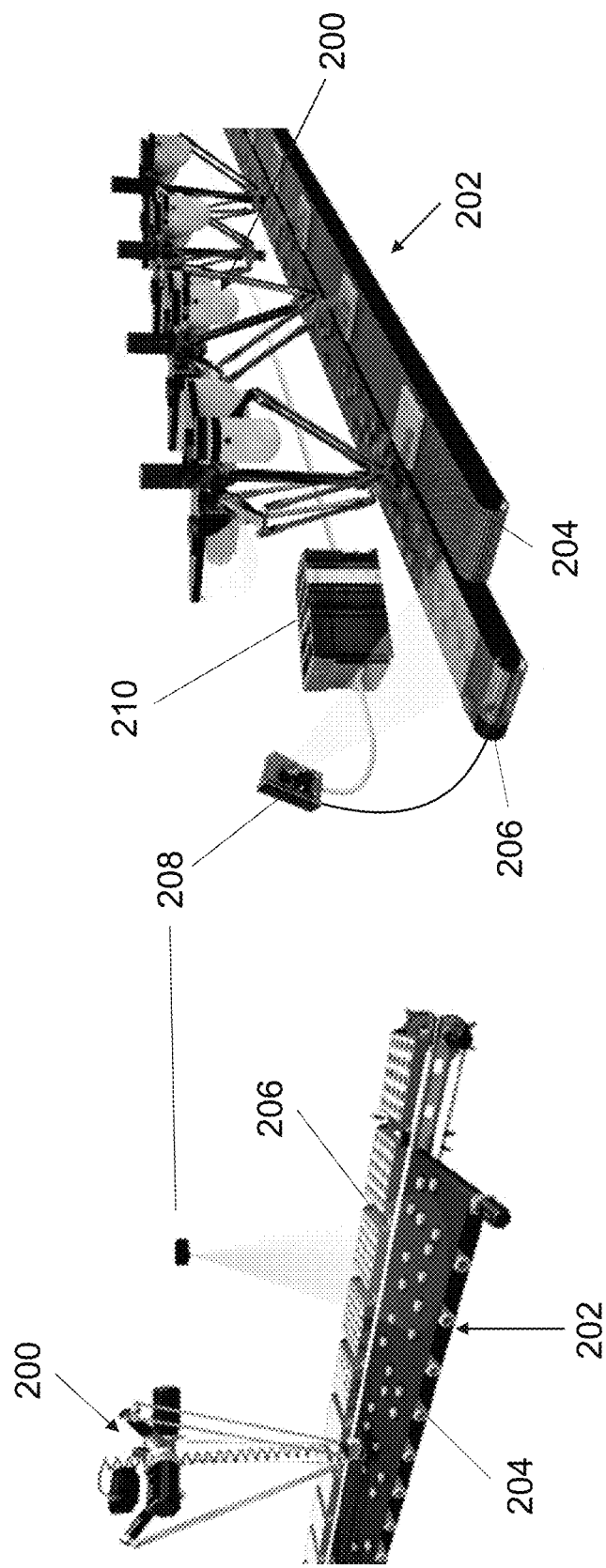
FIGS. 26 and 27 show a schematic and a photograph respectively of a robot picker on a classification and sorting line according to embodiments of the present invention.

FIGS. 26 and 27 show a schematic and an example of a pick and place delta robot 200 integrated into an automated sorting line 202 with conveyors 204 and 206, and camera 208. Camera may be connected to other components 210 of a vision system.

In the present embodiments, the delta robot 200 has a suction unit, and then it either sucks the mosquitoes directly lying on the belt and puffs them into release boxes to fill the boxes, or the robot may suck the mosquitoes from nets on which the mosquitoes are standing, as per some of the above embodiments.

Reference is now made to FIG. 28, which is a simplified diagram showing an embodiment in which the females are identified and zapped and the males are collected. A container with water and pupae 280 is provided, along with a camera 282 for imaging emerging adults for classification and a laser 284 for zapping the females. Air flow from fan 286 blows the surviving adults through duct 288 past camera 290 or other sensor which counts the passing mosquitoes. Container 292 collects the mosquitoes and is exchanged for a new container 294 when the count determines that it is full.

Figure 29:
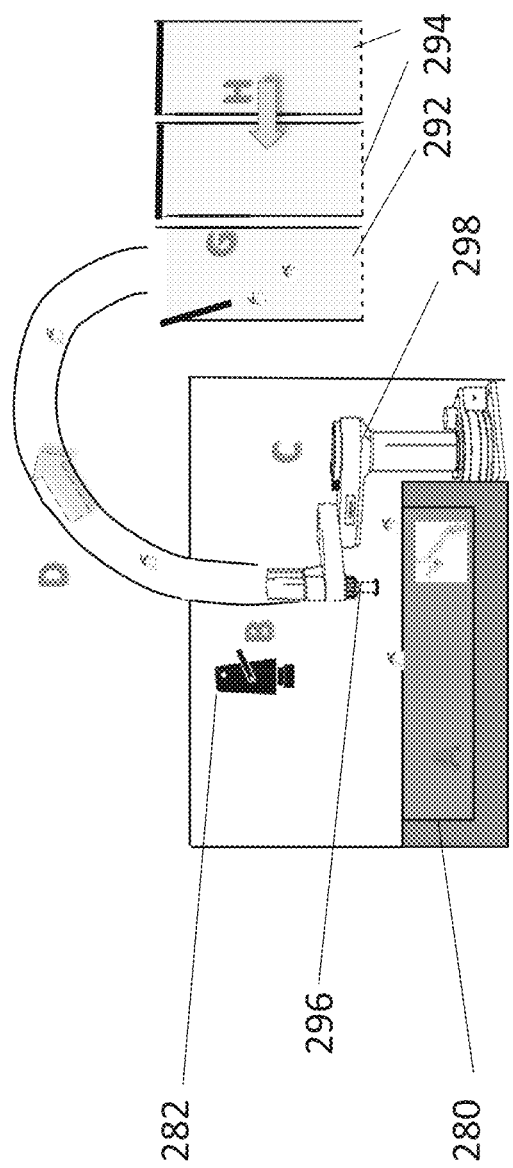

Reference is now made to FIG. 29, which is a simplified diagram of an embodiment that differs from the version in FIG. 28. Here the males are identified and actively sucked up. Parts that are the same as in the previous embodiment are given the same reference numerals and are not described again except as needed for an understanding of the present embodiment. A container with water and pupae 280 is provided, along with a camera 282 for imaging emerging adults for classification. A suction tube 296 is provided on the end of a robot arm 298 to actively suck the males through duct 288. Container 292 collects the mosquitoes and is exchanged for a new container 294 when full.

Figure 30:
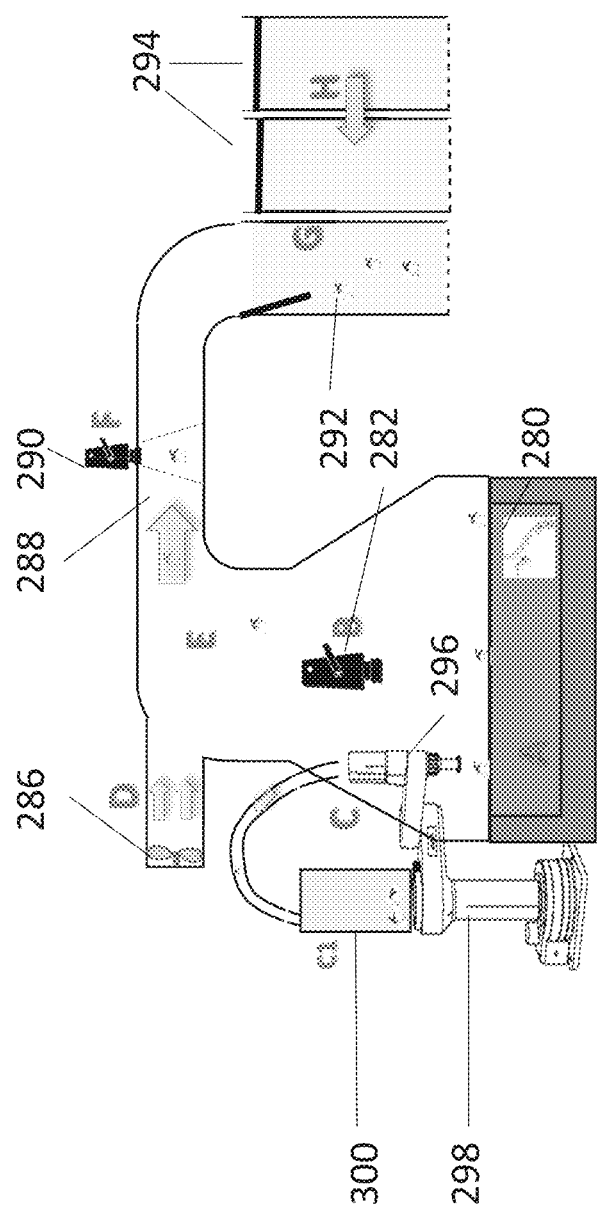

Reference is now made to FIG. 30, which is a simplified diagram of an embodiment that differs from the version in FIG. 28. Here the males are left to fly for collection, whereas the females are actively sucked into a separate container. Parts that are the same as in the previous embodiment are given the same reference numerals and are not described again except as needed for an understanding of the present embodiment. A container with water and pupae 280 is provided, along with a camera 282 for imaging emerging adults for classification. A suction tube 296 is provided on the end of a robot arm 298 to actively suck the females into container 300. The males fly and get into the airstream driven by fan 286 to be driven through duct 288 past camera 290 or other sensor which counts the passing mosquitoes. Container 292 collects the mosquitoes and is exchanged for a new container 294 when the count determines that it is full.

Figure 31:
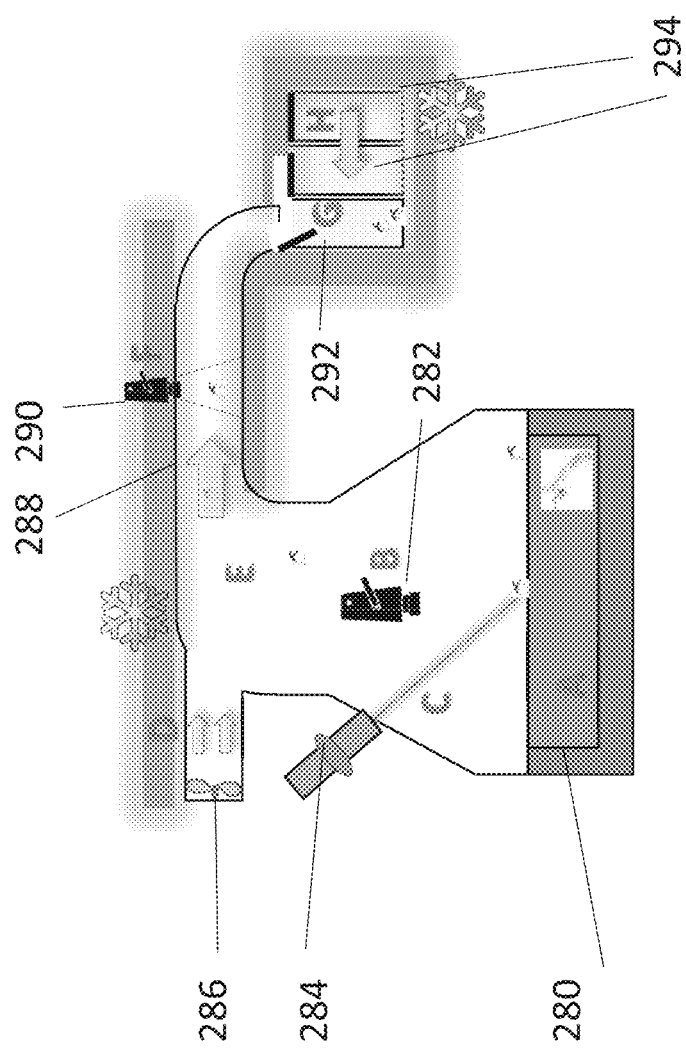

Reference is now made to FIG. 31, which is a simplified diagram of a further embodiment of the present invention. As with FIG. 28, the females are zapped by a laser and the males are left to fly into an airstream. Parts that are the same as in the previous embodiment are given the same reference numerals and are not described again except as needed for an understanding of the present embodiment. A container with water and pupae 280 is provided, along with a camera 282 for imaging emerging adults for classification. Laser 284 is directed to zap females. The males are left to fly and get into the airstream driven by fan 286 to be driven through duct 288 past camera 290 or other sensor which counts the passing mosquitoes. Container 292 collects the mosquitoes and is exchanged for a new container 294 when the count determines that it is full. Duct 288 and the containers are actively cooled to slow down the mosquitoes so that more can be packed into a single container.

Figure 32:
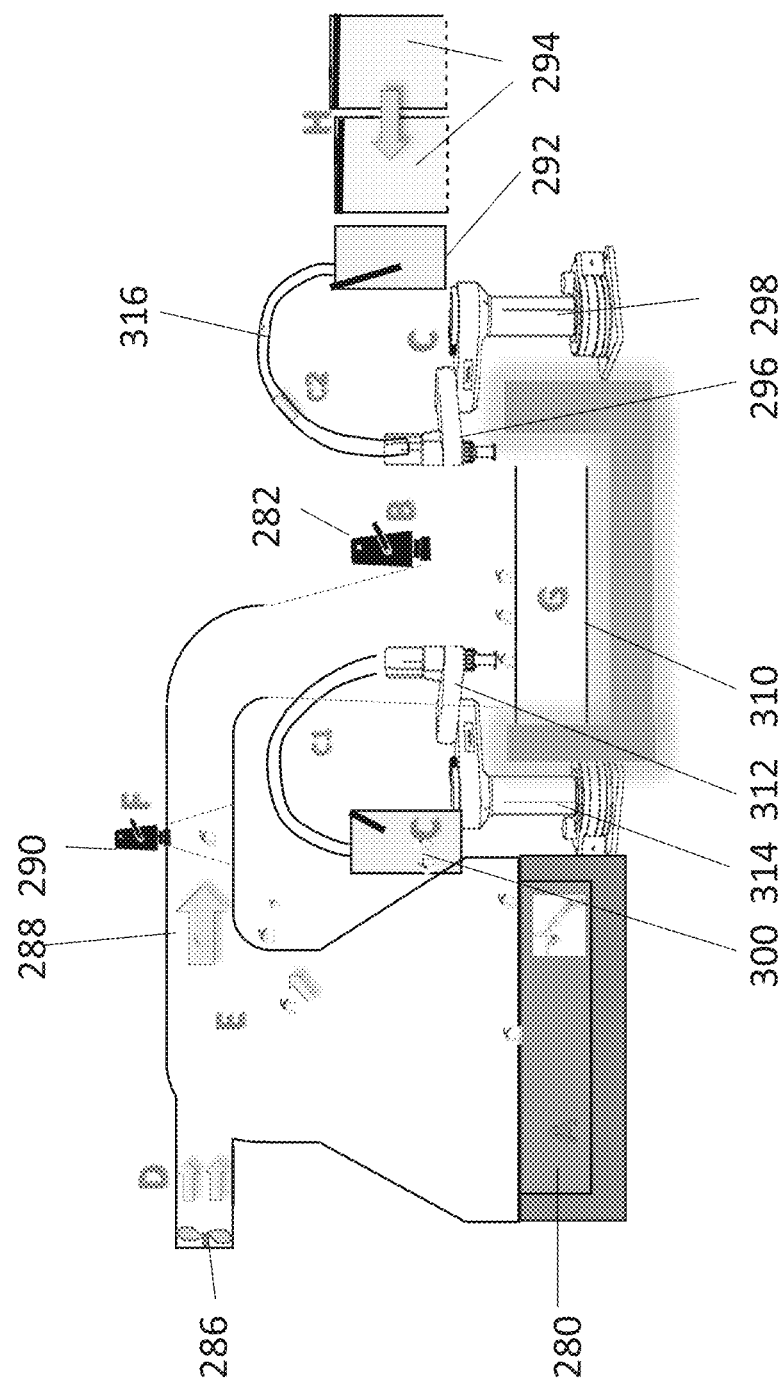

Reference is now made to FIG. 32, which is a simplified diagram of a further embodiment of the present invention. In this embodiment, all emerging insects fly away from the pupa dish and are brought to a selection area where they are cooled and thus immobilized. Then the males and females are separated. Parts that are the same as in the previous embodiment are given the same reference numerals and are not described again except as needed for an understanding of the present embodiment. A container with water and pupae 280 is provided, All emerging adults are left to fly and get into the airstream driven by fan 286 to be driven through duct 288 past camera 290 or other sensor which counts the passing mosquitoes to selecting surface 310 which is cooled. Above cooled selecting surface 310 is camera 282 for imaging emerging adults for classification. A suction tube 296 is provided on the end of a robot arm 298 to actively suck the males through tube or duct 316 into container 292. A second suction tube 312 is operated by second robot arm 314 to suck the females into container 300. Container 292 collects the mosquitoes and is exchanged for a new container 294 when the count determines that it is full. The count from second robot arm 314 may be subtracted from the count at camera 290 to give the number of males being introduced into container 292. Duct 288 and the containers may also be actively cooled as before.

It will be appreciated that any of the previous embodiments may be used to carry out the sorting, and females may be zapped or left in place as males are removed etc.

Figure 33:
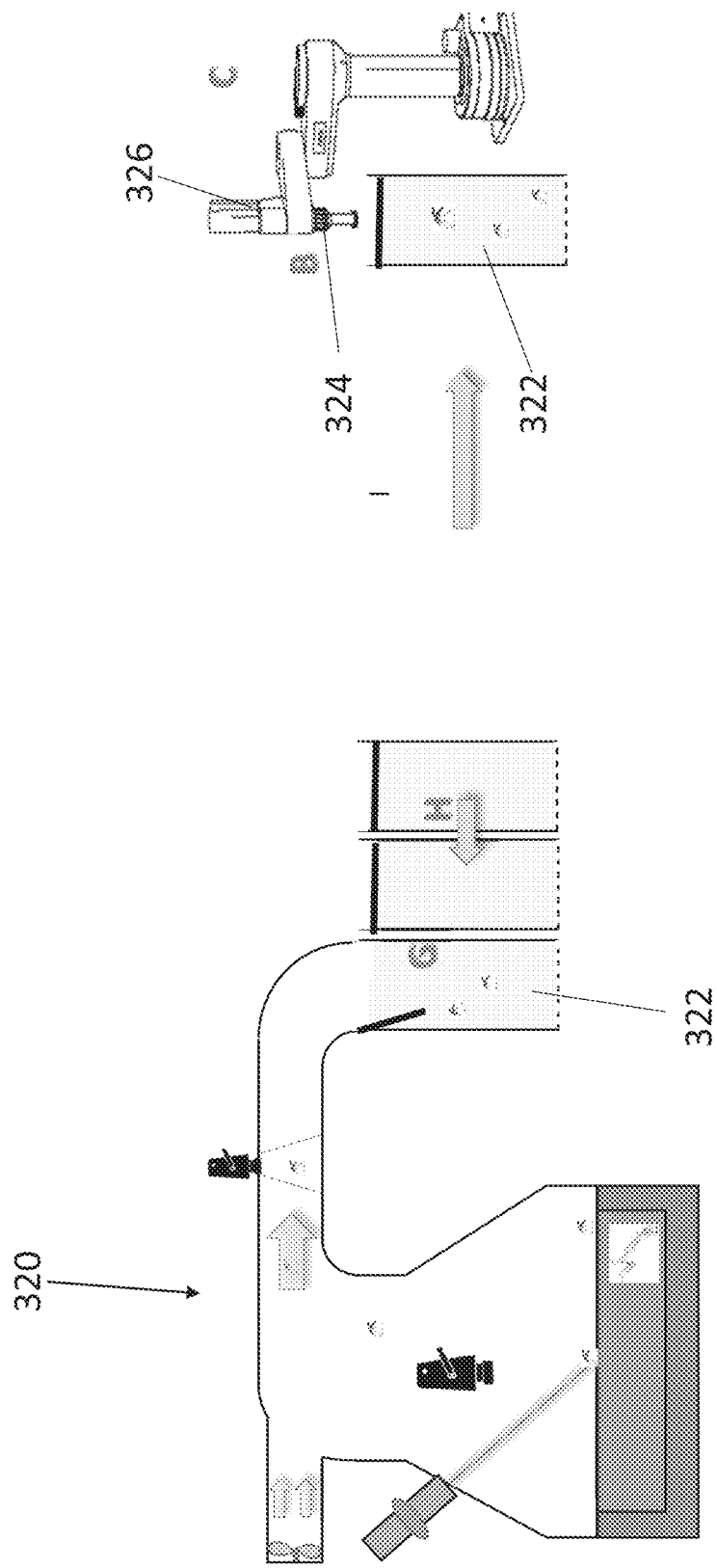
FIG. 33 is a simplified diagram showing how the insects in a full container according to the present embodiments may be fed.

Reference is now made to FIG. 33, which is a simplified diagram showing how the insects may be fed when in the containers. The sorting and filling station 320 provides containers 322 full of mosquitoes. The full containers are transferred for storage, and have feeding holes or a feeding net on one surface 324. Feeding robot 326 spreads sugar water or the like on the surface 324 to feed the insects. It is expected that during the life of a patent maturing from this application many relevant robot picking, vision and learning technologies will be developed and the scopes of the corresponding terms are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. Method for sex-sorting of mosquitoes by physically extracting a class of mosquitoes from unsorted mosquitoes, the method comprising:
   obtaining said unsorted mosquitoes;
   obtaining images and coordinates of individuals of said unsorted mosquitoes at an imaging location;
   electronically classifying said individuals from said images into at least one member of a group of classifications including male mosquitoes and female mosquitoes;
   using a mechanism to physically add to a storage individual insects corresponding to images of one classification and to physically remove individual insects corresponding to images of another classification, said removing using said obtained coordinates, thereby to provide a storage device containing the sex-sorted mosquitoes of one class alone for subsequent distribution, wherein said unsorted mosquitoes are one member of the group consisting of emerging pupae and adults, and wherein if said member is emerging pupae then said images are obtained following emergence, and if said member is adults, then said images are obtained while said adults are in a cooled or non-flying state.

2. The method of claim 1, wherein said classifying comprises using a trained neural network.

3. The method of claim 2, wherein said trained neural network comprises four or more layers.

4. The method of claim 2, wherein said obtaining images comprises obtaining successive frames, generating differences between said successive frames and using said differences to track individuals.

5. The method according to claim 1, comprising tracking movement of individual mosquitoes prior to using said mechanism.

6. The method according to claim 5, comprising obtaining said images for classification using a first, relatively high resolution, camera, and carrying out said tracking using a second, relatively low resolution, camera.

7. The method according to claim 1, wherein said identified individuals are of said male class and said identified individuals are picked off and placed in storage or wherein said identified individuals are of said female class and said identified individuals are destroyed or picked off.

8. The method of claim 7, wherein said mechanism comprises a suction device or a blower device or a robot arm to pick off said identified individuals and place in storage, or a zapper or a suction device or a blowing device for removing said identified individuals.

9. The method according to claim 8, wherein said zapper is one member of the group comprising an electrode and a laser.

10. The method according to claim 1, wherein, if an individual is not classified into male or female by a predetermined time, then the image is sent to an operator or wherein if an individual is not classified as male by a predetermined time then it is classified as female.

11. The method according to claim 1, wherein said mosquitoes are cooled in a container having walls, so that the cooled mosquitoes stand on an interior side of said walls, the method comprising dismantling said box to present said interior sides of said walls for said obtaining said images.

12. The method according to claim 1, wherein said mosquitoes are cooled in a container having a door and said door is opened onto a first moving conveyor, to allow said cooled mosquitoes to fall through, said first moving conveyor carrying said mosquitoes to an imaging location for said obtaining images, and said conveyor stopping with mosquitoes at said imaging location.

13. The method according to claim 12, wherein said first moving conveyor is a relatively fast moving conveyor, thereby to prevent piling of mosquitoes disrupting imaging, wherein said identified individuals are of the female class so that male mosquitoes are retained on the conveyor, the first moving conveyor emptying onto a second moving conveyor being a relatively slow moving conveyor, said relatively slow moving conveyor conveying said retained mosquitoes for placing in storage cartridges.

14. Apparatus for sex-sorting of mosquitoes by physically extracting a class of mosquitoes from unsorted mosquitoes, the apparatus comprising:
   a source of unsorted mosquitoes;
   a camera configured to obtain images of individual mosquitoes at an imaging location;

a classifier, configured to electronically classify said individuals from said images into at least one member of a group of classifications including male mosquitoes and female mosquitoes;

a mechanism associated with said classifier and configured to physically reach an individual insect classified into one of said members, the mechanism to store or physically remove said individual insects according to a respective classification, said physically removing comprising operating said mechanism on said insects of said respective classification, thereby to provide a storage physically containing sex-sorted mosquitoes of a single class only;

a first moving conveyor leading to said camera and said mechanism and;

a container with a door and a cooler, wherein said mosquitoes are cooled in said container and said door is opened onto said first moving conveyor, to allow said cooled mosquitoes to fall through, said first moving conveyor carrying said mosquitoes to an imaging location below said camera for said obtaining images.

15. The apparatus of claim 14, wherein said classifier comprises a trained neural network.

16. The apparatus of claim 15, wherein said trained neural network comprises four or more layers.

17. The apparatus of claim 14, wherein a camera is configured to obtain successive frames, and a processor attached to said camera generates difference frames between said successive frames and using said difference frames to identify individuals.

18. The apparatus according to claim 14, wherein said classifier is configured with a recurrent neural network (RNN).

19. The apparatus according to claim 14, wherein said unsorted mosquitoes are emerging pupae and said images are obtained following emergence.

20. The apparatus according to claim 14, further comprising a cooler, and wherein said unsorted mosquitoes are adults and said images are obtained and said mosquitoes are cooled.

21. The apparatus according to claim 14, further comprising a tracker configured to track movement of individual mosquitoes prior to using said mechanism.

22. The apparatus according to claim 21, wherein said camera is a relatively high resolution, camera, and said tracker is a second, relatively low resolution, camera.

23. The apparatus of claim 14, wherein said mechanism comprises a robot arm or a suction device or a blower device to pick off said identified individuals or a zapper for destroying said identified individuals.

24. The apparatus according to claim 23, wherein said zapper is one member of the group comprising an electrode, a solenoid and a laser.

25. The apparatus according to claim 14, comprising a container with detachable walls associated with a cooler, wherein said mosquitoes are cooled in said container, so that the cooled mosquitoes stand on an interior side of said walls, and the box is dismantable to present said interior sides of said walls for said obtaining said images.

26. The apparatus according to claim 14, further comprising a second moving conveyor and storage cartridges, wherein said first moving conveyor is a relatively fast moving conveyor, thereby to prevent piling of mosquitoes disrupting imaging, wherein male mosquitoes are retained on the conveyor, the first moving conveyor configured to empty onto said second moving conveyor, said second moving conveyor being a relatively slow moving conveyor, said second moving conveyor configured to convey said retained mosquitoes for placing in storage cartridges.

27. Apparatus for sex-sorting of adult mosquitoes by physically extracting a class of mosquitoes from unsorted mosquitoes, the apparatus comprising:

a source of unsorted adult mosquitoes;

a camera configured to obtain images of individual adult mosquitoes;

a classifier, configured to electronically classify said individuals from said images into at least one member of a group of classifications including male mosquitoes and female mosquitoes;

a physical mechanism associated with said classifier and configured to physically reach an individual adult mosquito, which mosquito has been classified into one of said members, the mechanism to physically store or remove said individuals according to a respective classification, thereby to provide a storage physically containing sex-sorted mosquitoes of one classification only, wherein the camera is located to take images of said adult mosquitoes when the adult mosquitoes are in a non-flying state a first moving conveyor leading to said camera and said mechanism and;

a container with a door and a cooler, wherein said mosquitoes are cooled in said container and said door is opened onto said first moving conveyor, to allow said cooled mosquitoes to fall through, said first moving conveyor carrying said mosquitoes to an imaging location below said camera for said obtaining images.

28. The apparatus of claim 27, wherein said obtaining images is accompanied by obtaining coordinates, and said physically storing or removing of individuals according to a respective one of said classifications comprises operating said mechanism using respectively obtained coordinates.

29. The apparatus according to claim 27, configured to track movement of individual mosquitoes prior to using said mechanism.

30. The apparatus according to claim 27, wherein said identified individuals are of said male class, said physical mechanism being configured to pick off said identified individuals and place said identified individuals in said storage or wherein said identified individuals are of said female class, said physical mechanism being configured to destroy or remove said identified individuals.

31. The apparatus of claim 30, wherein said physical mechanism comprises a suction device or a blower device or a robot arm to pick off said identified individuals and place in storage, or a zapper or a suction device or a blowing device for removing said identified individuals.

32. The apparatus according to claim 31, wherein said zapper is one member of the group comprising an electrode and a laser.

33. The apparatus according to claim 27, comprising a duct leading from said source of adult mosquitoes to said classifier, and configured for said insects to walk towards said classifier.

34. Method for sex-sorting of adult mosquitoes by physically extracting a class of mosquitoes from unsorted mosquitoes, the method comprising:

obtaining a source of unsorted adult mosquitoes;

obtaining images of individual adult mosquitoes when said insects are in a non-flying state;

electronically classifying said individuals from said images into at least one member of a group of classifications including male mosquitoes and female mosquitoes;

mechanically reaching an individual adult mosquito, which mosquito has been classified into one of said members;

physically storing or removing said individuals according to a respective classification, thereby to provide a storage physically containing sex-sorted mosquitoes of one classification only, wherein said unsorted mosquitoes are one member of the group consisting of emerging pupae and adults, and wherein if said member is emerging pupae then said images are obtained following emergence, and if said member is adults, then said images are obtained while said adults are in a cooled or non-flying state.

35. The method according to claim 34, comprising tracking movement of individual mosquitoes prior to using said mechanical reaching.

36. The method according to claim 34, wherein said identified individuals are of said male class and said identified individuals are picked off and placed in storage or wherein said identified individuals are of said female class and said identified individuals are destroyed or picked off.

37. The method of claim 34, wherein said mechanically reaching comprises using a suction device or a blower device or a robot arm to pick off said identified individuals and place in storage, or a zapper or a suction device or a blowing device for removing said identified individuals.

38. The method according to claim 37, wherein said zapper is one member of the group comprising an electrode and a laser.

39. The method according to claim 37, comprising walking said insects through a duct leading from said source of adult mosquitoes to be classified.

40. Method for sex-sorting of mosquitoes by physically extracting a class of mosquitoes from unsorted mosquitoes, the method comprising:

obtaining said unsorted mosquitoes;

obtaining images and of said unsorted mosquitoes at an imaging location;

electronically classifying said individuals from said images into at least one member of a group of classifications including male mosquitoes and female mosquitoes;

using a mechanism to physically add to a storage individual insects corresponding to images of one classification and to physically destroy or remove individual insects corresponding to images of another classification, thereby to provide a storage device containing the sex-sorted mosquitoes of one class alone for subsequent distribution, wherein said unsorted mosquitoes are one member of the group consisting of emerging pupae and adults, and wherein if said member is emerging pupae then said images are obtained following emergence, and if said member is adults, then said images are obtained while said adults are in a cooled or non-flying state.

* * * * *